(12) United States Patent
Dria et al.

(10) Patent No.: US 11,278,458 B2
(45) Date of Patent: Mar. 22, 2022

(54) CRIMPED FIBER SPUNBOND NONWOVEN WEBS/LAMINATES

(71) Applicant: The Procter & Gamble Company, Cincinnati, OH (US)

(72) Inventors: Ray Dennis Dria, Mason, OH (US); Urmish Popatlal Dalal, Milford, OH (US); Kevin Ronald Kanya, Liberty Township, OH (US); Kelyn Anne Arora, Cincinnati, OH (US); Stephanie Niezgoda Moss, Cincinnati, OH (US); Shirdish Poondru, Cincinnati, OH (US); Timothy Ian Mullane, Union, KY (US); Nathan Ray Whitely, Liberty Township, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 378 days.

(21) Appl. No.: 15/937,180

(22) Filed: Mar. 27, 2018

(65) Prior Publication Data
US 2018/0271717 A1    Sep. 27, 2018

Related U.S. Application Data

(60) Provisional application No. 62/476,892, filed on Mar. 27, 2017.

(51) Int. Cl.
*A61F 13/15* (2006.01)
*A61F 13/49* (2006.01)
(Continued)

(52) U.S. Cl.
CPC .. *A61F 13/49012* (2013.01); *A61F 13/15203* (2013.01); *A61F 13/49009* (2013.01);
(Continued)

(58) Field of Classification Search
CPC .......... A61F 13/49014; A61F 13/49015; A61F 2013/49022; A61F 2013/49023;
(Continued)

(56) References Cited

U.S. PATENT DOCUMENTS 3,113,225 A    12/1963    Kleesattel et al.
3,338,992 A    8/1967    Allison
(Continued)

FOREIGN PATENT DOCUMENTS

CN    102573724 A    7/2012
CN    103434239 B    11/2015
(Continued)

OTHER PUBLICATIONS

International Search Report, PCT/US2018/024549, dated May 30, 2018, 13 pages.
(Continued)

*Primary Examiner* — Catharine L Anderson
(74) *Attorney, Agent, or Firm* — Sarah M. DeCristofaro; Wednesday G. Shipp

(57) ABSTRACT

An article includes a chassis having a topsheet, backsheet and an absorbent core disposed between the topsheet and backsheet; and an ear joined to the chassis. The ear includes a ring-rolled laminate having a first nonwoven web and an elastomeric film; wherein the first nonwoven web has a crimped spunbond fiber nonwoven web.

18 Claims, 12 Drawing Sheets

(51) Int. Cl.

| | | |
|---|---|---|
| *A61F 13/514* | (2006.01) | |
| *A61L 15/22* | (2006.01) | |
| *A61L 15/24* | (2006.01) | |
| *A61L 15/60* | (2006.01) | |
| *D04H 3/007* | (2012.01) | |
| *D04H 3/018* | (2012.01) | |
| *D04H 3/16* | (2006.01) | |
| *A61F 13/513* | (2006.01) | |

(52) U.S. Cl.
CPC .. *A61F 13/49011* (2013.01); *A61F 13/49014* (2013.01); *A61F 13/49015* (2013.01); *A61F 13/514* (2013.01); *A61L 15/225* (2013.01); *A61L 15/24* (2013.01); *A61L 15/60* (2013.01); *D04H 3/007* (2013.01); *D04H 3/018* (2013.01); *D04H 3/16* (2013.01); *A61F 2013/15284* (2013.01); *A61F 2013/15292* (2013.01); *A61F 2013/15406* (2013.01); *A61F 2013/15552* (2013.01); *A61F 2013/15869* (2013.01); *A61F 2013/4903* (2013.01); *A61F 2013/49022* (2013.01); *A61F 2013/49034* (2013.01); *A61F 2013/49084* (2013.01); *A61F 2013/49093* (2013.01); *A61F 2013/51338* (2013.01); *D10B 2321/022* (2013.01); *D10B 2509/026* (2013.01)

(58) Field of Classification Search
CPC .. A61F 2013/49034; A61F 2013/49084; A61F 2013/15292; A61F 2013/15325
See application file for complete search history.

(56) References Cited

U.S. PATENT DOCUMENTS

| | | | |
|---|---|---|---|
| 3,562,041 A | 2/1971 | Robertson | |
| 3,566,726 A | 3/1971 | Politis | |
| 3,692,613 A | 9/1972 | Pederson | |
| 3,733,238 A | 5/1973 | Long et al. | |
| 3,802,817 A | 4/1974 | Matsuki | |
| 3,848,594 A | 11/1974 | Buell | |
| 3,849,241 A | 11/1974 | Butin | |
| 3,860,003 A | 1/1975 | Buell | |
| 3,911,173 A | 10/1975 | Sprague, Jr. | |
| 3,929,135 A | 12/1975 | Thompson | |
| 4,116,892 A | 9/1978 | Schwarz | |
| 4,324,314 A | 4/1982 | Beach et al. | |
| 4,405,297 A | 9/1983 | Appel | |
| 4,463,045 A | 7/1984 | Ahr et al. | |
| 4,573,986 A | 3/1986 | Minetola et al. | |
| 4,610,678 A | 9/1986 | Weisman | |
| 4,629,643 A | 12/1986 | Curro et al. | |
| 4,634,440 A | 1/1987 | Widlund et al. | |
| 4,662,875 A | 5/1987 | Hirotsu | |
| 4,673,402 A | 6/1987 | Weisman | |
| 4,780,352 A | 10/1988 | Palumbo | |
| 4,785,996 A | 11/1988 | Ziecker et al. | |
| 4,834,735 A | 5/1989 | Alemany | |
| 4,834,741 A | 5/1989 | Sabee | |
| 4,842,666 A | 6/1989 | Werenicz | |
| 4,846,815 A | 7/1989 | Scripps | |
| 4,854,984 A | 8/1989 | Ball | |
| 4,888,231 A | 12/1989 | Angstadt | |
| 4,892,536 A | 1/1990 | DesMarais et al. | |
| 4,894,060 A | 1/1990 | Nestegard | |
| 4,919,738 A | 4/1990 | Ball et al. | |
| 4,940,464 A | 7/1990 | Van Gompel et al. | |
| 4,946,527 A | 8/1990 | Battrell | |
| 4,990,147 A | 2/1991 | Freeland | |
| 5,006,394 A | 4/1991 | Baird | |
| 5,037,416 A | 8/1991 | Allen | |
| 5,092,861 A | 3/1992 | Nomura et al. | |
| 5,137,537 A | 8/1992 | Herron | |
| 5,143,679 A | 9/1992 | Weber et al. | |
| 5,147,345 A | 9/1992 | Lavon | |
| 5,149,720 A | 9/1992 | DesMarais et al. | |
| 5,151,092 A | 9/1992 | Buell | |
| 5,156,793 A | 10/1992 | Buell et al. | |
| 5,167,897 A | 12/1992 | Weber et al. | |
| 5,221,274 A | 6/1993 | Buell et al. | |
| 5,242,436 A | 9/1993 | Weil | |
| 5,246,433 A | 9/1993 | Hasse et al. | |
| 5,260,345 A | 11/1993 | Desmarais | |
| 5,266,392 A | 11/1993 | Land | |
| 5,269,775 A | 12/1993 | Freeland | |
| 5,342,338 A | 8/1994 | Roe | |
| 5,360,420 A | 11/1994 | Cook et al. | |
| 5,382,400 A | 1/1995 | Pike | |
| 5,387,207 A | 2/1995 | Dyer | |
| 5,397,316 A | 3/1995 | Young | |
| 5,418,045 A | 5/1995 | Pike | |
| 5,422,172 A | 6/1995 | Wu | |
| 5,433,715 A | 7/1995 | Tanzer et al. | |
| 5,518,801 A | 5/1996 | Chappell et al. | |
| 5,554,145 A | 9/1996 | Roe et al. | |
| 5,569,234 A | 10/1996 | Buell et al. | |
| 5,571,096 A | 11/1996 | Dobrin | |
| 5,580,411 A | 12/1996 | Nease et al. | |
| 5,591,155 A * | 1/1997 | Nishikawa | A61F 13/49015 604/385.22 |
| 5,599,335 A | 2/1997 | Goldman et al. | |
| 5,607,414 A | 3/1997 | Richards et al. | |
| 5,607,760 A | 3/1997 | Roe | |
| 5,609,587 A | 3/1997 | Roe | |
| 5,622,772 A | 4/1997 | Stokes | |
| 5,628,097 A | 5/1997 | Benson et al. | |
| 5,635,191 A | 6/1997 | Roe | |
| 5,643,588 A | 7/1997 | Roe | |
| 5,658,639 A | 8/1997 | Curro et al. | |
| 5,665,300 A | 9/1997 | Brignola | |
| 5,674,216 A | 10/1997 | Buell et al. | |
| 5,700,254 A | 12/1997 | McDowall et al. | |
| 5,702,551 A | 12/1997 | Huber et al. | |
| 5,707,468 A | 1/1998 | Arnold | |
| 5,817,199 A | 10/1998 | Brennecke et al. | |
| 5,827,909 A | 10/1998 | DesMarais | |
| 5,865,823 A | 2/1999 | Curro | |
| 5,897,545 A | 4/1999 | Kline et al. | |
| 5,916,661 A | 6/1999 | Benson et al. | |
| 5,957,908 A | 9/1999 | Kline et al. | |
| 5,968,025 A | 10/1999 | Roe et al. | |
| 5,972,806 A | 10/1999 | Weinberger et al. | |
| 5,993,432 A | 11/1999 | Lodge | |
| 6,004,306 A | 12/1999 | Robles et al. | |
| 6,030,373 A | 2/2000 | Vangompel | |
| 6,036,796 A | 3/2000 | Halbert et al. | |
| 6,096,668 A | 8/2000 | Abuto | |
| 6,107,537 A | 8/2000 | Elder | |
| 6,118,041 A | 9/2000 | Roe et al. | |
| 6,120,487 A | 9/2000 | Ashton | |
| 6,120,489 A | 9/2000 | Johnson et al. | |
| 6,123,792 A | 9/2000 | Samida | |
| 6,140,551 A | 10/2000 | Niemeyer | |
| 6,153,209 A | 11/2000 | Vega et al. | |
| 6,169,151 B1 | 1/2001 | Waymouth | |
| 6,255,236 B1 | 7/2001 | Cree | |
| 6,369,121 B1 | 4/2002 | Catalfamo et al. | |
| 6,410,129 B2 | 6/2002 | Zhang et al. | |
| 6,426,444 B2 | 7/2002 | Roe et al. | |
| 6,432,098 B1 | 8/2002 | Kline | |
| 6,454,989 B1 * | 9/2002 | Neely | D04H 3/007 264/555 |
| 6,458,447 B1 | 10/2002 | Cabell et al. | |
| 6,465,073 B1 | 10/2002 | Morman | |
| 6,472,045 B1 | 10/2002 | Morman | |
| 6,472,084 B1 | 10/2002 | Middlesworth et al. | |
| 6,475,600 B1 | 11/2002 | Morman | |
| 6,498,284 B1 | 12/2002 | Roe | |
| 6,508,641 B1 | 1/2003 | Kubik | |
| 6,513,221 B2 | 2/2003 | Vogt | |
| 6,518,378 B2 | 2/2003 | Waymouth | |
| 6,534,149 B1 | 3/2003 | Daley et al. | |

(56) References Cited

U.S. PATENT DOCUMENTS

| | | |
|---|---|---|
| 6,540,854 B2 | 4/2003 | Couillard |
| 6,555,643 B1 | 4/2003 | Kieger |
| 6,559,262 B1 | 5/2003 | Waymouth |
| 6,572,595 B1 | 6/2003 | Klemp et al. |
| 6,572,598 B1 | 6/2003 | Ashton |
| 6,586,652 B1 | 7/2003 | Roe et al. |
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass et al. |
| 6,645,569 B2 | 11/2003 | Cramer et al. |
| 6,649,001 B2 | 11/2003 | Heden |
| 6,677,258 B2 | 1/2004 | Carroll et al. |
| 6,692,477 B2 | 2/2004 | Gibbs |
| 6,713,159 B1 | 3/2004 | Blenke et al. |
| 6,758,925 B1 | 7/2004 | Stegelmann |
| 6,767,420 B2 | 7/2004 | Stegelmann |
| 6,825,393 B2 | 11/2004 | Roe et al. |
| 6,830,800 B2 | 12/2004 | Curro |
| 6,843,134 B2 | 1/2005 | Anderson et al. |
| 6,861,571 B1 | 3/2005 | Roe et al. |
| 6,863,933 B2 | 3/2005 | Cramer et al. |
| 6,878,433 B2 | 4/2005 | Curro |
| 6,974,514 B2 | 12/2005 | Hamulski |
| 7,056,404 B2 | 6/2006 | McFall et al. |
| 7,062,983 B2 | 6/2006 | Anderson et al. |
| 7,108,759 B2 | 9/2006 | You |
| 7,112,621 B2 | 9/2006 | Rohrbaugh et al. |
| 7,270,861 B2 | 9/2007 | Broering et al. |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda et al. |
| 7,572,249 B2 | 8/2009 | Betts |
| 7,582,075 B2 | 9/2009 | Betts |
| 7,625,363 B2 | 12/2009 | Yoshimasa et al. |
| 7,741,235 B2 | 6/2010 | Hashimoto et al. |
| 7,803,244 B2 | 9/2010 | Siqueira |
| 7,806,883 B2 | 10/2010 | Fossum et al. |
| 7,819,853 B2 | 10/2010 | Desai et al. |
| 7,824,594 B2 | 11/2010 | Qureshi et al. |
| 7,870,651 B2 | 1/2011 | Middlesworth |
| 7,896,641 B2 | 3/2011 | Qureshi et al. |
| 7,917,985 B2 | 4/2011 | Dorsey et al. |
| 7,931,632 B2 | 4/2011 | Betts |
| 7,954,213 B2 | 6/2011 | Mizutani et al. |
| 7,998,127 B2 | 8/2011 | Betts |
| 8,062,279 B2 | 11/2011 | Miyamoto |
| 8,062,572 B2 | 11/2011 | Qureshi et al. |
| 8,092,438 B2 | 1/2012 | Betts |
| 8,118,801 B2 | 2/2012 | Macura et al. |
| 8,158,043 B2 | 4/2012 | Gibson et al. |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani et al. |
| 8,454,571 B2 | 6/2013 | Rezai et al. |
| 8,480,642 B2 | 7/2013 | Betts |
| 8,491,557 B2 | 7/2013 | Kline |
| 8,491,742 B2 | 7/2013 | Waas et al. |
| 8,496,775 B2 | 7/2013 | Deng et al. |
| 8,502,013 B2 | 8/2013 | Zhao et al. |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | O'Donnell et al. |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck |
| 8,940,116 B2 | 1/2015 | Gilgenbach |
| 9,102,132 B2 | 8/2015 | Wennerbck |
| 9,211,221 B2 | 12/2015 | Macura |
| 9,301,889 B2 | 4/2016 | Miyamoto |
| 9,358,161 B2 | 6/2016 | Lawson |
| 9,434,143 B2 | 9/2016 | Sablone |
| 9,498,941 B2 | 11/2016 | Sablone |
| 9,533,067 B2 | 1/2017 | Schonbeck |
| 9,687,580 B2 | 6/2017 | Schonbeck |
| 9,724,248 B2 | 8/2017 | Hughes |
| 9,821,542 B2 | 11/2017 | Bruce |
| 10,524,964 B2 | 1/2020 | Sauer |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 | 12/2002 | Kline |
| 2003/0021951 A1 | 1/2003 | Desai et al. |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0233082 A1 | 12/2003 | Kline et al. |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0224132 A1 | 11/2004 | Roe |
| 2005/0008839 A1 | 1/2005 | Cramer et al. |
| 2005/0065487 A1 | 3/2005 | Graef et al. |
| 2005/0107764 A1 | 5/2005 | Matsuda et al. |
| 2005/0154362 A1 | 7/2005 | Warren et al. |
| 2005/0245162 A1 | 11/2005 | Mccormack |
| 2005/0287892 A1 | 12/2005 | Fouse |
| 2006/0035055 A1 | 2/2006 | Schnelder et al. |
| 2006/0062963 A1 | 3/2006 | Middlesworth |
| 2006/0135024 A1 | 6/2006 | Thomas |
| 2006/0148361 A1 | 7/2006 | Mccormack |
| 2006/0149209 A1 | 7/2006 | Malchow |
| 2006/0247567 A1 | 11/2006 | Baldauf et al. |
| 2006/0287637 A1 | 12/2006 | Lam |
| 2007/0105472 A1 | 5/2007 | Marche |
| 2007/0123124 A1 | 5/2007 | Middlesworth |
| 2007/0142798 A1 | 6/2007 | Goodlander et al. |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0051748 A1 | 2/2008 | Black |
| 2008/0076315 A1 | 3/2008 | Mccormack |
| 2008/0119102 A1 | 5/2008 | Hughes |
| 2008/0147031 A1 | 6/2008 | Long et al. |
| 2008/0241476 A1 | 10/2008 | Olguin |
| 2008/0305298 A1 | 12/2008 | Lakshmi |
| 2008/0312622 A1 | 12/2008 | Hundorf et al. |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko et al. |
| 2009/0258210 A1 | 10/2009 | Iyad et al. |
| 2009/0275909 A1 | 11/2009 | Sakaguchi |
| 2009/0292266 A1 | 11/2009 | Bäck |

(56) References Cited

U.S. PATENT DOCUMENTS

| | | |
|---|---|---|
| 2009/0294044 A1 | 12/2009 | Gill et al. |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2009/0326492 A1* | 12/2009 | Hietpas .......... A61F 13/42 604/361 |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0268183 A1 | 10/2010 | Een |
| 2010/0280481 A1 | 11/2010 | Kline |
| 2011/0004176 A1 | 1/2011 | Andersson |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0152812 A1 | 6/2011 | Hird |
| 2011/0178490 A1 | 7/2011 | Lavon |
| 2011/0196332 A1 | 8/2011 | Cheng |
| 2011/0318987 A1 | 12/2011 | Ooishi |
| 2012/0045620 A1 | 2/2012 | Oba et al. |
| 2012/0055613 A1 | 3/2012 | Back |
| 2012/0055615 A1 | 3/2012 | Back |
| 2012/0061015 A1 | 3/2012 | Lavon et al. |
| 2012/0061016 A1 | 3/2012 | Lavon et al. |
| 2012/0095429 A1 | 4/2012 | Kobayashi et al. |
| 2012/0100351 A1 | 4/2012 | Covelli |
| 2012/0116342 A1 | 5/2012 | Stjernholm |
| 2012/0141742 A1 | 6/2012 | Yamaguchi et al. |
| 2012/0143165 A1 | 6/2012 | Macura et al. |
| 2012/0168063 A1 | 7/2012 | Beuther |
| 2012/0196091 A1 | 8/2012 | Mizutani et al. |
| 2012/0209230 A1 | 8/2012 | Mansfield |
| 2012/0238980 A1 | 9/2012 | Lam |
| 2012/0251771 A1 | 10/2012 | Wilson |
| 2012/0277713 A1 | 11/2012 | Raycheck et al. |
| 2012/0316526 A1 | 12/2012 | Rosati et al. |
| 2012/0321839 A1 | 12/2012 | Uematsu et al. |
| 2013/0017370 A1 | 1/2013 | Yamaguchi et al. |
| 2013/0022784 A1 | 1/2013 | Uematsu et al. |
| 2013/0072887 A1 | 3/2013 | LaVon et al. |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi et al. |
| 2013/0164480 A1 | 6/2013 | Sakurai et al. |
| 2013/0165883 A1 | 6/2013 | Kimura et al. |
| 2013/0178815 A1 | 7/2013 | Ohashi et al. |
| 2013/0184665 A1 | 7/2013 | Kato et al. |
| 2013/0211356 A1 | 8/2013 | Nishikawa et al. |
| 2013/0213547 A1 | 8/2013 | Schneider et al. |
| 2013/0218116 A1 | 8/2013 | Schneider et al. |
| 2013/0230700 A1 | 9/2013 | Schoenbeck |
| 2013/0236700 A1 | 9/2013 | Yamanaka et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0289512 A1* | 10/2013 | Rhodes ............ A61F 13/4963 604/385.24 |
| 2013/0306226 A1 | 11/2013 | Zink et al. |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke et al. |
| 2014/0135194 A1 | 5/2014 | Sablone |
| 2014/0148774 A1 | 5/2014 | Brown et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0234575 A1 | 8/2014 | Mitsuno et al. |
| 2014/0330232 A1 | 11/2014 | Schönbeck |
| 2014/0377506 A1 | 12/2014 | Eckstein et al. |
| 2014/0377513 A1 | 12/2014 | Galie et al. |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas et al. |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle et al. |
| 2016/0013614 A1 | 1/2016 | Moto |
| 2016/0136014 A1 | 5/2016 | Arora |
| 2016/0166443 A1* | 6/2016 | Arora .............. A61F 13/5116 604/378 |
| 2016/0167334 A1 | 6/2016 | Arora et al. |
| 2016/0206485 A1 | 7/2016 | Seitz |
| 2016/0270972 A1 | 9/2016 | Surushe |
| 2016/0324697 A1 | 11/2016 | Schoenbeck |
| 2017/0027775 A1 | 2/2017 | Barnes |
| 2017/0056256 A1 | 3/2017 | Smith |
| 2017/0079851 A1 | 3/2017 | Greening, II |
| 2017/0079854 A1 | 3/2017 | Butler |
| 2017/0087029 A1 | 3/2017 | Nelson et al. |
| 2017/0142806 A1 | 5/2017 | Park |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal |
| 2018/0042778 A1 | 2/2018 | Lenser et al. |
| 2018/0042779 A1 | 2/2018 | Lenser |
| 2018/0042780 A1 | 2/2018 | Leaser |
| 2018/0042784 A1 | 2/2018 | Koshijima |
| 2018/0042785 A1 | 2/2018 | Dalal et al. |
| 2018/0042786 A1 | 2/2018 | Mueller |
| 2018/0042787 A1 | 2/2018 | Lenser et al. |
| 2018/0271716 A1 | 9/2018 | Dalal |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2020/0170846 A1 | 6/2020 | Lenser |
| 2020/0179179 A1 | 6/2020 | Lenser |
| 2020/0268563 A1 | 8/2020 | Lenser |

FOREIGN PATENT DOCUMENTS

| | | |
|---|---|---|
| CN | 104837455 B | 4/2018 |
| EP | 1256594 A1 | 11/2002 |
| EP | 1447066 A1 | 8/2004 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 2647360 B1 | 6/2018 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012524645 A | 10/2012 |
| JP | 6240733 B1 | 11/2017 |
| JP | 2017065142 A | 11/2018 |
| WO | WO9510996 | 4/1995 |

(56) References Cited

FOREIGN PATENT DOCUMENTS

| | | |
|---|---|---|
| WO | WO9511652 | 5/1995 |
| WO | 9516746 A1 | 6/1995 |
| WO | 9828123 A1 | 7/1998 |
| WO | WO0045763 | 8/2000 |
| WO | WO200059430 A1 | 10/2000 |
| WO | 0073031 A1 | 12/2000 |
| WO | WO02067809 A2 | 9/2002 |
| WO | 2003007864 A1 | 1/2003 |
| WO | 2004017882 A2 | 3/2004 |
| WO | 2004017885 A1 | 3/2004 |
| WO | WO2004060652 A1 | 7/2004 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | WO2008156075 A1 | 12/2008 |
| WO | 2009146307 A1 | 12/2009 |
| WO | WO2010055699 A1 | 5/2010 |
| WO | WO2010118214 A1 | 10/2010 |
| WO | 2010126415 A1 | 11/2010 |
| WO | 2011080643 A2 | 7/2011 |
| WO | WO2011125893 A1 | 10/2011 |
| WO | WO2012052172 | 4/2012 |
| WO | 2012030571 A3 | 5/2012 |
| WO | 2012112501 A1 | 8/2012 |
| WO | WO2012137553 A1 | 10/2012 |
| WO | 2012154318 A1 | 11/2012 |
| WO | 2013027390 A1 | 2/2013 |
| WO | WO2013018846 A1 | 2/2013 |
| WO | WO2013047890 A1 | 4/2013 |
| WO | 2013132403 A1 | 9/2013 |
| WO | 2013163141 A1 | 10/2013 |
| WO | WO2013157365 A1 | 10/2013 |
| WO | WO2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | 2016073713 A1 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

Extended European Search Report and Search Opinion; Application No. 20183749.9 dated Nov. 9, 2020; 8 pages.
International Search Report and Written Opinion; Application No. PCT/US2020/070219 dated Oct. 1, 2020; 14 pages.
PCT International Search Report, Appl. No. PCT/US2017/046388, dated Sep. 22, 2017, 15 pages.
PCT International Search Report and Written Opinion, Appl. No. PCT/US2017/046393, dated Sep. 25, 2017, 16 pages.
PCT International Search Report, Appl. No. PCT/US2017/046394, dated Sep. 28, 2017, 15 pages.
PCT International Search Report, Appl. No. PCT/US2017/046395, dated Sep. 20, 2017, 15 pages.
All Office Actions, U.S. Appl. No. 15/674,559.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
International Search Report, Appl. No. PCT/US2017/046397, dated Sep. 28, 2017, 13 pages.
All Office Actions, U.S. Appl. No. 15/674,561.
International Search Report, Appl. No. PCT/US2019/024011, dated Jul. 4, 2019, 14 pages.
EP Application No. 17754982.1, Third Party Observation, dated Jun. 17, 2020, 9 pages.
EP Application No. 17764961.3, Third Party Observation, dated Aug. 24, 2020, 6 pages.
Interational Search Report, Appl. No. PCT/US2017/046398, dated Sep. 28, 2017, 13 pages.
International Search Report, Appl. No. PCT/US2017/049026, dated Oct. 19, 2017, 13 pages.
U.S. Appl. No. 16/916,655, filed Jun. 30, 2020, Nelson Edward Greening, II et al.
Unpublished U.S. Appl. No. 15/937,180, filed Dec. 1, 2020, to Ray Dennis Dria et al.
All Office Actions, U.S. Appl. No. 17/108,212.

* cited by examiner

CRIMPED FIBER SPUNBOND NONWOVEN WEBS/LAMINATES

FIELD OF THE INVENTION

The disclosure herein relates to a crimped spunbond fiber nonwoven web and an article incorporating the nonwoven web.

BACKGROUND OF THE INVENTION

Elastomeric laminates are used in various products including absorbent articles (e.g., diapers, incontinence articles, feminine hygiene pads). Such laminates typically include an elastomeric layer that provides extensibility to the laminate and an outer layer that is less stretchable but suitable for providing durability and desirable tactile properties. In this way, the laminate permits a component of an article to closely and comfortably contact the wearer while providing desirable exterior qualities.

Elastomeric laminates can be produced by multiple methods. For example, the laminate may be in the form a gathered laminate, wherein the coverstock layer forms rugosities when the elastic layer is relaxed. Said gathered laminates may be formed by extending the elastic layer material to a greater extent than the outer material at the time of lamination. Alternatively, the outer layer material may be corrugated and the elastic material may be in its relaxed state at the time of lamination. In either scenario, following lamination, the coverstock gathers or bunches and forms rugosities when the laminate is in a relaxed state.

Another type of elastomeric laminate is a zero strain laminate. During lamination, the outer and elastic layers are joined at approximately zero relative strain (i.e., both layers are relaxed at approximately zero strain). Zero strain laminates are activated by a mechanical straining process, which creates separations or deformations in the outer layer materials and renders the laminate elastic. Nonwoven webs are typically used as the outer layer in such laminates. Nonwovens may be formed by various techniques, many of which may have drawbacks with respect to forming laminates. For instance, nonwoven webs made of carded staple fibers are typically easily extensible, offering little resistance during mechanical activation, but said carded nonwovens are expensive. On the other hand, spunbond nonwovens are relatively inexpensive but tend to be more difficult to extend without tearing. In addition, spunbond webs typically lack the softness of carded nonwovens.

Therefore, there is a need for a laminate that includes a nonwoven having adequate extensibility and strength properties. There is a further need for reducing costs and increasing efficiency in creating elastomeric laminates. There is also a need to provide elastomeric laminates with desirable softness and texture.

SUMMARY OF THE INVENTION

The present invention addresses one or more of the foregoing needs. In one form, an article comprises a chassis having a topsheet, backsheet and an absorbent core disposed between the topsheet and backsheet; and an ear joined to the chassis. The ear may comprise a ring-rolled laminate having a first nonwoven web and an elastomeric film, wherein the first nonwoven web comprises a crimped spunbond fiber nonwoven web. In another form, an article comprises a chassis having a topsheet, a backsheet and an absorbent core disposed between the topsheet and backsheet; and an ear joined to the chassis. The ear may comprise a laminate having a first nonwoven, a second nonwoven and an elastomeric film disposed between the first and second nonwovens, wherein the laminate further comprises a plurality of ultrasonic bonds. The first nonwoven comprises a first crimped spunbond nonwoven web and the laminate may comprise an Average Extension at 2N of about 5 mm or greater according to the Extension Test Method herein. In certain embodiments, an elastic laminate has one or more nonwoven webs and an elastomeric film. At least one nonwoven web comprises an external surface and an interior surface opposite the external surface, wherein the interior surface faces the elastomeric film. Said nonwoven also comprises a crimped spunbond nonwoven layer, and the crimped spunbond nonwoven layer forms the external surface. The external surface may comprise an Average TS7 softness value of about 7 dB V2rms or less as determined by the Softness Test Method herein.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
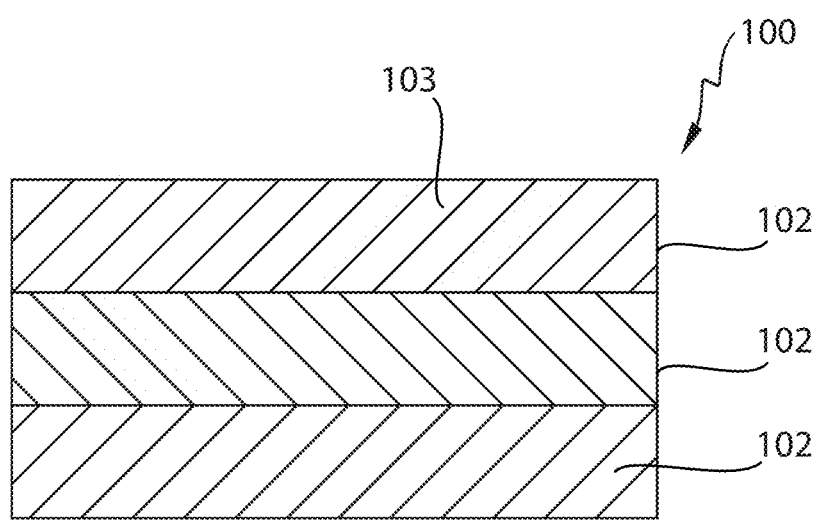
FIG. 1 is a schematic representation of a nonwoven laminate of the present invention shown in an cross sectional view of the nonwoven laminate.

"Absorbent article", refers to devices which absorb and contain body exudates, and, more specifically, refers to devices which are placed against or in proximity to the body of the wearer to absorb and contain the various bodily exudates discharged from the body. The term absorbent article includes, but is not limited to, diapers, pants, training pants, adult incontinence products, sanitary napkins, tampons, wipes, and liners.

"Activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. Activation processes are disclosed for example in U.S. Pat. Pub. No. 2013/0082418, U.S. Pat. Nos. 5,167,897 and 5,993,432. "Activated" refers to a material that has been subjected to activation.

A "ring-rolled" or "ring-rolled activated" component has been activated by a ring-rolling system as is described U.S. Pat. No. 5,156,793 or 5,167,897 or by a High Speed Research Press (HSRP) as described in U.S. Pat. Nos. 7,062,983 and 6,843,134 issued to Anderson et al.

"Bi-component fibers" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement.

"Bi-constituent fibers" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In other examples, a bi-component fiber may comprise a multi-constituent components.

"Elastic," "elastomeric," and "elastically extensible" mean the ability of a material to stretch by at least 100% without rupture or breakage at a given load, and upon release of the load the elastic material or component exhibits at least 80% recovery (i.e., has less than 20% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

"Fibrils" refers to projections, elongate projections, bumps that extend outwardly from a surface or generally radially outwardly from an outer surface of a fiber. In some instances, the projections, elongate projections, or bumps may extend radially outwardly relative to a longitudinal axis of the fiber. Radially outwardly means in the range of 1 to 89 degrees relative to the longitudinal axis. In still other instances, the projections, elongate projections, or bumps may extend radially outwardly from a surface of a fiber at least in a longitudinal central third of the fiber. The projections, elongate projections, or bumps comprise, consist of, or consist essentially of (e.g., 51% to 100% or 51% to 99%), melt additives. The projections, elongate projections, or bumps grow from the fibers post-nonwoven substrate formation only after a time period (e.g., 6-100 hours) under ambient conditions. Fibrils can be viewed using an SEM at, at least 1,000 times magnification.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Monocomponent fiber" refers to a fiber formed from one extruder using one or more polymers. This is not meant to exclude fibers formed from one polymer to which small amounts of additives have been added for coloration, antistatic properties, opacity, lubrication, hydrophilicity, etc.

"Nonwoven web" refers to a web having a structure of individual fibers or threads which are interlaid, but not in a repeating pattern as in a woven or knitted fabric, which do not typically have randomly oriented fibers. The basis weight of nonwoven fabrics is usually expressed in grams per square meter (gsm). The basis weight of a nonwoven web is the combined basis weight of the constituent layers and any other added components. Fiber diameters are usually expressed in microns; fiber size can also be expressed in denier, which is a unit of weight per length of fiber.

As used herein "philic" and "phobic" have meanings as well established in the art with respect to the contact angle of a referenced liquid on the surface of a material. Thus, a material having a liquid contact angle of greater than about 75 degrees is considered phobic, and a material having a liquid contact angle of less than about 75 degrees is considered philic.

"Spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 8 and 40 microns.

"Crimped fibers" or "crimped spunbond fibers" refers to bi-component spunbond fibers having a crimp, which fibers may be configured in a side-by-side, core-eccentric sheath or other suitable configuration. The selection of suitable resin combinations and bi-component fiber configuration can lead to a helical crimp or curl generated in the fibers. "Crimp" refers to the undulation, curling, or waves in a fiber. FIG. 1A is a photograph of a crimped spunbond fiber, while FIG. 1B is a photograph of a straight, noncrimped fiber. The crimp may occur spontaneously during the spinning or laydown process, on its own after web formation. In some instances, crimp may be induced mechanically or chemically during fiber making or processing. Crimping may be helical, plannar, or combination of the two. The purpose of crimping fibers is to increase the volume per fiber, which in turn helps improve softness of the substrate made with crimped fibers. Microscopic or SEM analysis is often used to evaluate whether fibers have a crimped.

By "randomly oriented" it is meant that, due to processing conditions of a nonwoven layer, there may be a higher amount of fibers oriented in the machine direction (MD) than the cross direction (CD), or vice-versa.

"Machine direction" or "MD" is the direction parallel to the direction of travel of the web in a manufacturing process. The machine direction is typically the longitudinal direction of a component, such as an ear of an absorbent article. The "cross machine direction" or "CD" is the direction substantially perpendicular to the MD and in the plane generally defined by the web.

Laminates Comprising Crimped Spunbond Fiber Webs

Figure 2:
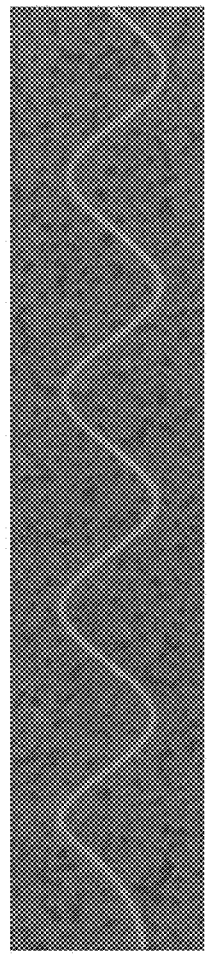
FIG. 2 is a photograph showing a crimped fiber.
Figure 3:
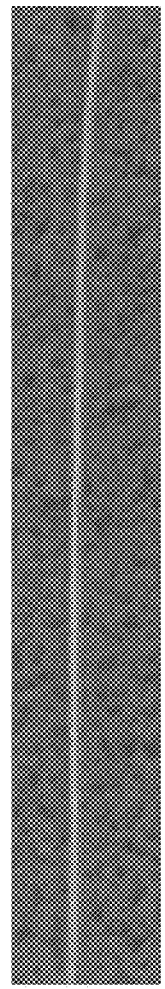
FIG. 3 is a photograph showing a straight fiber.

The present invention pertains to nonwoven webs comprising crimped spunbond fibers (i.e., a crimped spunbond fiber nonwoven web 100) and that are suitable for use in a disposable absorbent article. FIG. 1 is a schematic illustration of a nonwoven web according to the present invention. The web 100 includes multiple layers 102, one or more of which may comprise crimped spunbond fibers 103. FIG. 2 is a photograph of a crimped spunbond fiber, while FIG. 3 is a photograph of a straight fiber. Returning to FIG. 1, while shown to be rectangular, it is to be understood that the layers 102 and resultant web 100 are fibrous rather than smooth but are generally planar. In certain embodiments, the crimped spunbond fiber nonwoven web 100 may comprise a continuously crimped spunbond fiber nonwoven web, such that the web 100 comprises at least 80% crimped spunbond fibers by weight of the web. The web may comprise a majority of layers having crimped spunbond fibers. Additionally or alternatively, a layer within the crimped spunbond fiber nonwoven web 100 may comprise a continuously crimped spunbond fiber layer, such that the layer comprises at least 80% crimped spunbond fibers by weight of the layer 102. As discussed hereafter, the crimped spunbond fiber nonwoven webs and laminates comprising such webs may provide a softness benefit, an opacity benefit and/or may provide desirable extensibility and/or softness without compromising strength.

In some forms of the present invention, crimped spunbond fiber webs of the present invention may comprise multiple layers. For example, a crimped spunbond fiber web of the present invention may be made via a spunbond process comprising multiple spinbeams. In such forms, a first substrate created from a first spinbeam may comprise continuous spunbond fibers while a second substrate created from a second spinbeam may comprise continuous crimped spunbond fibers.

The nonwoven webs may comprise one or more different fiber layers. For instance, a nonwoven web may comprise one or more layers having spunbond crimped fibers and one or more layers formed by other methods (e.g., meltblown, carded, noncrimped spunbond (i.e., conventional spunbond), through air bonded or hydroentangled). The layers of a nonwoven web or a nonwoven web and adjacent layers in a disposable absorbent article may be bonded together using any bonding methods known to those of skill in the art, such as adhesive bonding, patterned adhesive coating, ultrasonic bonding, thermal bonding, mechanical bonding, or any combination of these bonding methods. The bonding may be done in a pattern of bonds or in arrays of bonds. The pattern may be a regular, uniform pattern or an irregular, non-uniform pattern. Bond patterns in one area of the web and/or article may differ from bond patterns in another area. If adhesive is used in the bonding process, the adhesive may be tinted, pigmented, and/or patterned.

The nonwoven web may be incorporated into a laminate. The laminate may comprise a film web and a crimped spunbond fiber nonwoven web (i.e., a web comprising spunbond crimped fibers). In other forms, the laminate may comprise one or more film layers, a crimped spunbond fiber nonwoven web and one or more additional nonwoven webs. Layers within the laminate may comprise the same dimensions (e.g., length, width, area) or one or more different dimensions. In some nonlimiting examples, laminates are elastomeric.

In various embodiments, the crimped spunbond fiber nonwoven webs may comprise an Average % Cross Direction Strain at Peak Force of about 50% or greater, or about 60% or greater, or from about 50% to about 200% according to the Tensile Test Method herein. Additionally or alternatively, the crimped spunbond fiber nonwoven web(s) utilized in the elastomeric laminate may comprise an Average Normalized Peak Force of about 0.17 N·m$^2$/g·cm or less, or about 0.12 N·m$^2$/g·cm or less, or about 0.08 N·m$^2$/g·cm or less, or from about 0.06 to about 0.18 N·m$^2$/g·cm according to the Tensile Test Method herein.

Figure 4:
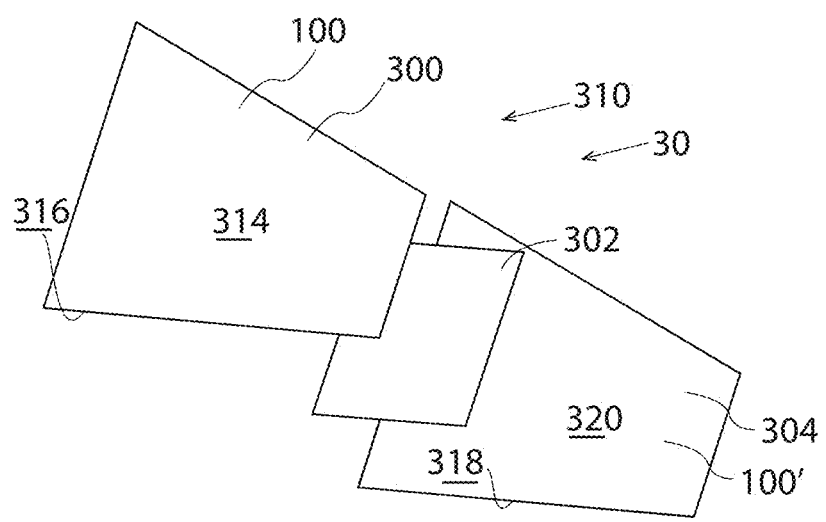
FIG. 4 is a schematic, exploded illustration of an exemplary elastomeric laminate in accordance with the present disclosure.

FIG. 4 schematically depicts an exemplary elastomeric laminate 310 that comprises a crimped spunbond fiber nonwoven web 100. In the nonlimiting example shown in FIG. 4, an ear 30 of an absorbent article comprises the elastomeric laminate. It is also contemplated that other components of an absorbent article may comprise the elastomeric laminate such as leg cuffs, waist bands and/or belts.

The elastomeric laminate may comprise a first nonwoven web 300 and an elastomeric layer 302 comprising one or more elastomeric materials. The first nonwoven web comprises a crimped spunbond fiber nonwoven web 100, having one or more layers 102 comprising crimped spunbond fibers 103. The first nonwoven web 300 may comprise additional nonwoven layers 102, such as conventional spunbond layers (S), nanofiber layers (N) and/or meltblown layers (M). The first nonwoven web may comprise any suitable configuration including but not limited to: SMS, SSS, SSMMS, SSMS, and SSMNMS. The first nonwoven web may be free of carded nonwoven layers or webs. The nonwoven layers in the first nonwoven web may be joined to one another by calendar bonds, as discussed in more detail below. The nonwoven web 300 may comprise a first external surface 314 and a first interior surface 316. The first interior surface 316 is substantially opposite the first external surface and faces the elastomeric layer 302. In certain embodiments, a crimped spunbond fiber nonwoven web 100 forms the external surface 314. In some nonlimiting examples, the first nonwoven web comprises a basis weight of about 25 gsm or less, or about 17 gsm or less, or about 14 gsm or less, or from about 10 gsm to about 25 gsm.

The elastomeric laminate may further comprises a second nonwoven web 304. The second nonwoven web may comprise one or more nonwoven layers 102 which may include spunbond layers, nanofiber layers and/or meltblown layers. The second nonwoven web may comprise a crimped spunbond fiber web 100', having one or more crimped spunbond fiber nonwoven layers. Alternatively, the second nonwoven web may be void of crimped spunbond fiber fibers. The second nonwoven web may comprise any suitable configuration including but not limited to: SMS, SSS, SSMMS, SSMS, and SSMNMS. The second nonwoven web may be free of carded nonwoven layers or webs. The second nonwoven web may comprise the same configuration as the first nonwoven web or a different configuration. Likewise, the second nonwoven web may comprise the same basis weight as the first nonwoven web or a different basis weight. Nonwoven layers in the second nonwoven web may be joined to one another by calendar bonds. The second nonwoven web 304 may comprise a second external surface 318 and a second interior surface 320. The second interior surface 320 is substantially opposite the second external surface and faces the elastomeric layer 302. In certain embodiments, a crimped spunbond fiber nonwoven web 100' forms the external surface 318.

Without being bound by theory, it is believed that carded layers, including carded crimped fibers, are not desirable given their expense and limitations compared to spunbond crimped fibers. Indeed, tensile strength for spunbond crimped fiber nonwoven webs may be greater than the tensile strength exhibited by carded crimped fiber nonwoven webs. In general, the spunbond process, including the spunbond crimped fiber process, utilizes continuous fibers while the carded spunbond fiber process utilizes staple fibers—fixed length not continuous. Still another distinction between crimped spunbond fiber nonwoven webs and crimped fiber carded nonwoven webs is that a tensile strength ratio between the MD and CD is generally more balanced for crimped spunbond fiber nonwoven webs. In general, crimped fiber carded nonwoven webs have a much higher tensile strength in the MD (versus the CD) as the fibers are typically combed to be aligned in the MD direction.

In certain embodiments, the elastomeric layer 302 is sandwiched between the first and second nonwoven layers 300, 304. The laminate layers may be joined by any suitable means. In some nonlimiting examples, the elastomeric layer is joined to the first and/or second nonwoven layers by ultrasonic bonding. In further nonlimiting, the elastomeric layer and nonwoven layer(s) are joined together by adhesive. Adhesive may be applied in amounts and at pressures suitable for binding laminate layers with adequate bond strength while allowing for processing of the laminate, such as ring-roll activation. For example, the skilled person will recognize that insufficient pressure when bonding the layers could lead to inadequate bond strength. Likewise, excessive pressure when bonding the layers could lead to holes or slits in the elastomeric layer, rigidity of the laminate, or other defects which would prevent processing such as ring-rolling or otherwise preclude elasticity in the final laminate.

The elastomeric layer may comprise one or more elastomeric materials which provide elasticity to at least a portion of said layer. Nonlimiting examples of elastomeric materials include film (e.g., styrenic block copolymer film, elastomeric polyolefin films, polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives, polyesters, polyurethanes, polyether amides, polyolefins, combinations thereof or any suitable known elastomers. Exemplary elastomers and/or elastomeric materials are disclosed in U.S. Pat. Nos. 8,618, 350; 6,410,129; 7,819,853; 8,795,809; 7,806,883; 6,677,258, 9,834,667, and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.), VERSIFY (homopolyolefins and random copolymers, and blends of random copolymers, available from Dow Chemical Company, Midland, Mich.), TAFMER (polyolefin elastomer available from Mitsui Chemicals), and INFUSE (olefin block copolymer, available from Dow Chemical, Midland Mich.).

Figure 5:
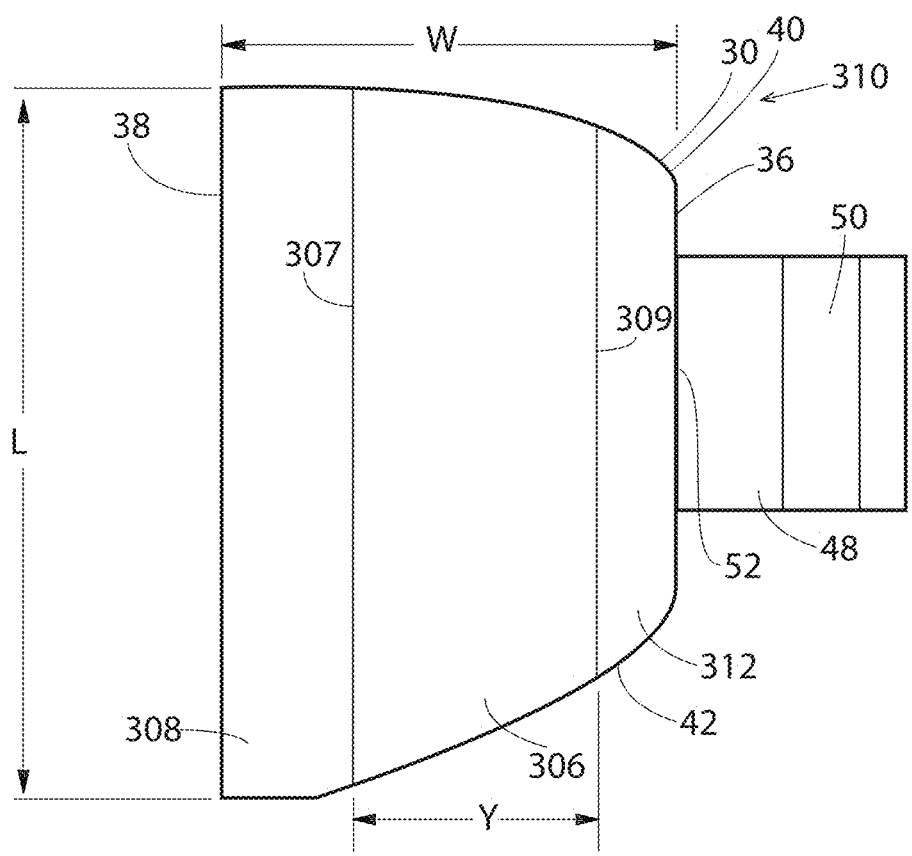
FIG. 5 is a schematic, plan illustration of an exemplary elastomeric laminate in accordance with the present disclosure.

In nonlimiting examples, the elastomeric layer comprises a film. The film may comprise a single layer or multiple layers. The film may be preactivated or unactivated. The film may be elastic in one or more directions. For example when incorporated into an absorbent article, the film may be elastic in the lateral and/or longitudinal direction of the article. The elastomeric layer may comprise a width, Y, as shown for example in FIG. 5. (FIG. 5 depicts an ear 30 which comprises an elastomeric laminate.) In some embodiments, Y is less than the width, W, of the laminate by at least about 10 mm. The elastomeric layer may have a length dimension that is the same as the laminate's length along with the entire width of the elastomeric layer, or a length dimension that is less than the length of the laminate at any point along with the width of the second layer. In some embodiments, the elastomeric layer may have a basis weight of from about 5 to about 150 gsm, or from about 10 to about 100 gsm, or less than about 150 gsm, reciting for each range every 5 gsm increment therein.

As also illustrated in FIG. 5, the laminate may comprise an elastic region 306. The elastic region 306 is generally defined by the perimeter of the elastomeric material. In the elastic region, the laminate is elastically extensible. In some embodiments, for example when an ear 30 comprises the laminate, the area of the elastic region comprises at least about 20% of, or from about 30% to about 80% of the total area of the laminate, reciting for said range every 5% increment therein. In further embodiments, Y (i.e., the maximum width of the elastomeric layer) is at least about 20% of, or from about 25% to about 85%, or from about 35% to about 80% of the total width, W, of the laminate, reciting for each range every 5% increment therein. The laminate further comprises one or more inelastic regions. In certain embodiments, the laminate comprises a first inelastic region 308, which extends laterally outward from the proximal edge 38 and is adjacent to the elastic region 306 at a first elastomeric material edge 307. The laminate may further include a second inelastic region 312, which may extend laterally inward from the distal side 36 and may be adjacent to the elastic region 306 at a second elastomeric material edge 309. The first and second inelastic regions may be made of the same material(s) or different materials.

In certain embodiments, the elastomeric laminate comprises a gathered laminate, wherein one of the layers is strained to a greater degree than a remaining layer during lamination. In this way, the relatively less extensible layer (i.e., the nonwoven) will form gathers when the laminate is in a relaxed state. In some embodiments, at least a portion of the elastomeric layer is strained while the nonwoven web(s) is/are in a relaxed state during lamination. The elastomeric layer may be stretched one or more directions. Corrugations then form in the nonwoven web(s) when the subsequently formed laminate is in a relaxed state. In nonlimiting examples, the elastomeric layer is stretched in a direction corresponding with the lateral direction of the article. In other words, when the laminate is joined to the chassis subsequent to lamination, it will be oriented such that the laminate is stretchable and/or elastic in the lateral direction of the article. In further nonlimiting examples, the laminate is also stretchable and/or elastic in the longitudinal direction.

Figure 6:
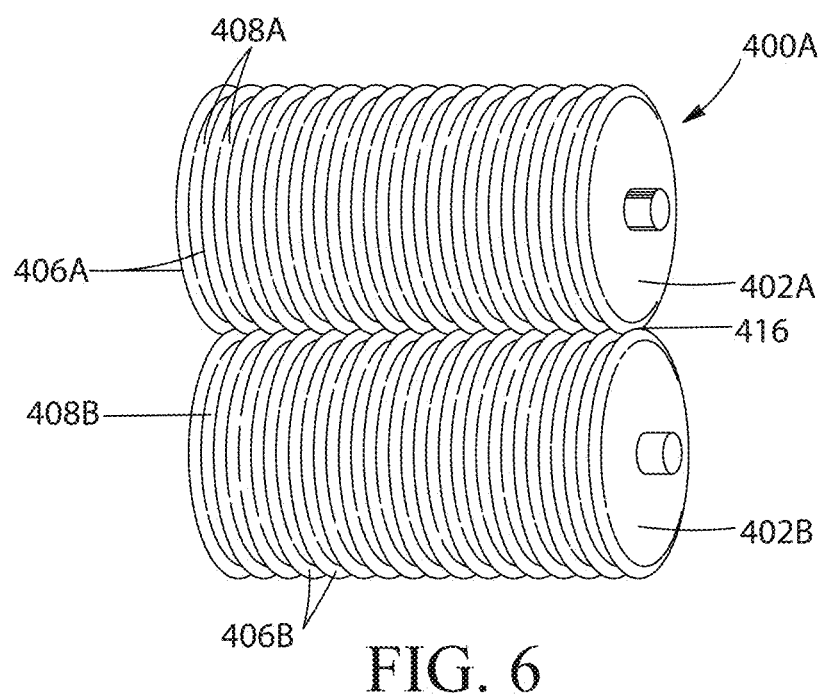
FIG. 6 is a schematic illustration of an apparatus for activating an elastomeric laminate of the present invention.

In certain embodiments, the elastomeric laminate is activated. In nonlimiting examples, the laminate may be activated by ring-rolling to enhance or provide elasticity to the laminate. The laminate may be provided to apparatus 400 shown in FIG. 6 for ring-rolling activation. As shown in FIG. 6, the apparatus 400 comprises two non-patterned grooved rolls 402A, 402B. The intermeshing features of the rolls 402A, 402B are each void of circumferentially-spaced teeth as is found in apparatuses used for creating tufts/caps as disclosed for example in U.S. Pat. No. 7,410,683. In operation, rolls 402A and 402B intermesh such that the ridges 406A of roll 402A extend into the grooves 408B of roll 402B and the ridges 406B of roll 402B extend into the grooves 408A of roll 402A. A nip 416 is formed between the counter-rotating intermeshing rolls 402A and 402B. Laminates may also be activated on a High Speed Research Press (HSRP) as described in U.S. Pat. Nos. 7,062,983 and 6,843,134 issued to Anderson et al. The HSRP process simulates ring-rolling activation with no measurable distinction between the identical laminates undergoing the two processes.

Activation in the described simulated ring rolling process refers to using aluminum plates with continuous intermeshing features (as opposed to roll system used in U.S. Pat. No. 5,156,793 or 5,167,897) to incrementally stretch portions of the laminate. Said continuous intermeshing features are void of circumferentially-spaced teeth.

In certain embodiments, the elastomeric laminate 310 may comprise an Air Permeability Value of at least about 1 $m^3/m^2/min$, or from about 2 $m^3/m^2/min$ to about 125 $m^3/m^2/min$, or from about 5 $m^3/m^2/min$ to about 35 $m^3/m^2/min$ according to the Air Permeability Test Method herein, reciting for each range every 1 $m^3/m^2/min$ increment therein.

In further embodiments, the elastomeric laminate may comprise an Average Peak Force at Break of about 20N or greater, or about 25N or greater, or about 30N or greater, or from about 20N to about 50N according to the Extension Test Method herein. In nonlimiting examples, the laminate comprises an adhesively bonded laminate having an Average Peak Force at Break of about 28N or greater, or about 30N or greater according to the Extension Test Method herein. Additionally or alternatively, the elastomeric laminate may comprise an adhesively bonded laminate; an Average Extension at 2N of about 15 mm or greater, or 20 mm about or greater, or from about 15 mm to about 25 mm according to the Extension Test Method herein; and/or an Average Extension at 4N of about 30 mm or greater, about 35 mm or greater, or from about 35 mm to about 50 mm according to the Extension Test Method herein. In other nonlimiting examples, the elastomeric laminate comprises an ultrasonically bonded laminate having an Average Peak Force at Break of about 26N or greater, or from about 25N to about 40N; an Average Extension at 2N of about 5 mm or greater, or 9 mm about or greater, or from about 5 mm to about 20 mm according to the Extension Test Method herein; and/or an Average Extension at 4N of about 25 mm or greater, about 30 mm or greater, or about 35 mm or greater according to the Extension Test Method herein.

In various embodiments, elastomeric laminates of the present invention may comprise one or more surfaces which comprise an Average TS7 value of about 10 dB $V^2$ rms or less, or about 7 dB $V^2$ rms or less, or about 5 dB $V^2$ rms or less, or from about 1 dB $V^2$ rms to about 10 dB $V^2$ rms, or from about 2 dB $V^2$ rms to about 8 dB $V^2$ rms according to the Softness Test Method herein, reciting for each range every 1 dB $V^2$ rms increment therein. Additionally or alternatively, the elastomeric laminate may comprise one or more surfaces with an Average TS750 value of about 100 dB V2 rms or less, or about 80 dB $V^2$ rms or less, or about 75 dB $V^2$ rms or less, or from about 50 dB $V^2$ rms to about 200 dB $V^2$ rms according to the Softness Test Method herein, reciting for each range every 1 dB $V^2$ rms increment therein. Lower TS7 and TS750 values indicate greater softness, which is highly desirable in absorbent articles. Consumers might find absorbent articles with high TS7 and TS750 values uncomfortable and/or scratchy or otherwise undesirable.

In some forms, the elastomeric laminate comprises the first nonwoven web 300, having an external surface 314 formed from a first crimped spunbond nonwoven web 100 as illustrated in FIG. 4. In such example, the external surface may comprise an Average TS7 value of about 10 dB $V^2$rms or less, or about 5 dB $V^2$rms or less, and/or an Average TS750 value of about 130 dB $V^2$rms or less, or of about 100 dB $V^2$rms or less 80 dB $V^2$rms or less as determined by the Softness Test Method herein. Additionally, or alternatively, the elastomeric laminate may comprise a second nonwoven web 304 having a second external surface 318. The second external surface 318 may be formed by a second crimped spunbond nonwoven web 100'. The second external surface may comprise any of the TS7 and/or TS750 values disclosed herein. In various embodiments, the laminate is free of carded nonwoven webs.

Examples of Nonwoven Webs and Elastomeric Laminates

Figure 7:
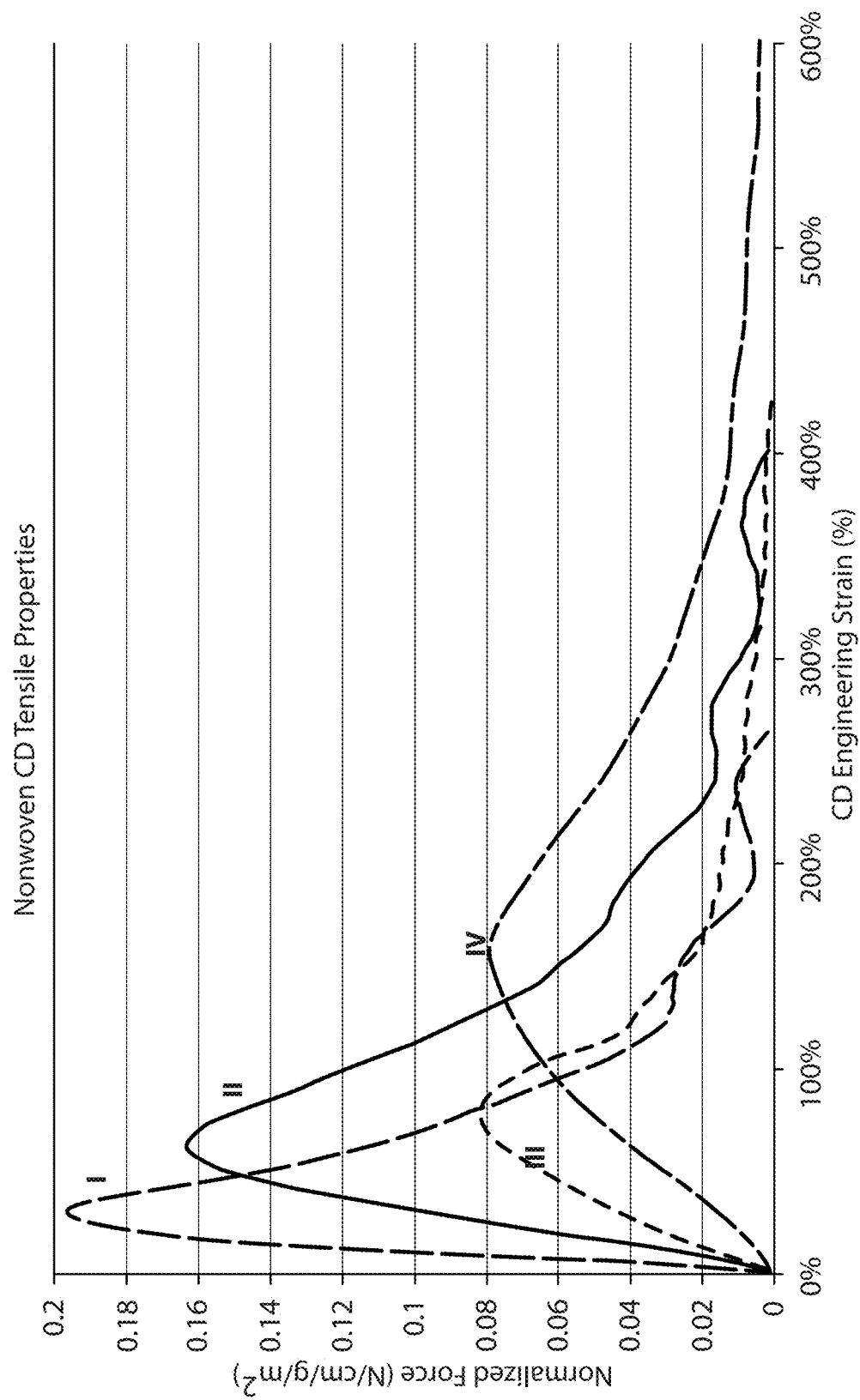
FIG. 7 is a chart depicting tensile properties of exemplary nonwoven webs.

FIG. 7 illustrates a comparison of nonwoven materials that may be utilized in elastomeric laminates. Comparative Nonwoven Example I is a nonwoven web having a basis weight of 14 gsm and a SSMMS configuration. Comparative Nonwoven Example I is commercially available from Avgol, USA under tradename AVMN1050678001. Comparative Nonwoven Example I is void of crimped spunbond nonwoven webs.

Crimped Spunbond Fiber Nonwoven Examples II-IV are nonwoven webs, which each have a basis weight of 25 gsm, a SS configuration, and each comprise two crimped spunbond nonwoven web layers. The crimped spunbond nonwoven webs comprise fibers of 1.7 denier per filament and side-by-side polypropylene/polypropylene bi-component fibers, where two different polypropylenes are used. Both polypropylene components comprise 4% of TiO2 masterbatch. Non-limiting examples of suitable commercially available polypropylene or polypropylene copolymers to be used as a component of the bi-component fibers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Moplen HP2833, HP462R and S, HP551R, HP552N, HP552R, HP553R, HP561R, HP563S, HP567P, HP568S, RP3231, Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC), and Achieve 3155 (a 35 melt flow rate Ziegler-Natta isotactic polypropylene from Exxon Mobil). Each nonwoven web was calendar bonded. Example II was calendar bonded with a dot bond pattern having 15% bond area. Example III was calendar bonded with an oval bond pattern having 18% bond area. Example IV was calendar bonded with a dot bond pattern having 12% bond area. The exemplary nonwoven webs were produced by Reifenhauser GmbH located in Troisdorf, Germany.

Table 1 shows examples of nonwoven webs, and FIG. 7 shows a comparison of tensile properties of said examples. As can be seen in Table 1 and FIG. 7, the inventive examples have lower Normalized Peak Force and greater % CD Strain at Peak Force than the comparative spunbond examples. Typically, such lower normalized peak force and higher % CD strain at peak values are achieved by using more expensive carded nonwovens. However, the present invention achieves carded nonwoven properties but at a much lower cost to deliver the needed elastic laminate properties for absorbent article comfort and conforming fit.

TABLE 1

Nonwoven Examples

| Example | Average Normalized Peak Force N · m²/g · cm | Average % CD Strain at Peak Force (%) |
|---|---|---|
| Comparative Nonwoven Example I | 0.197 ± 0.024 | 30.6 ± 1.5 |
| Crimped Spunbond Fiber Nonwoven Example II | 0.164 ± 0.010 | 61.4 ± 3.1 |
| Crimped Spunbond Fiber Nonwoven Example III | 0.082 ± 0.008 | 82.5 ± 13.8 |
| Crimped Spunbond Fiber Nonwoven Example IV | 0.079 ± 0.007 | 158.5 ± 10.7 |

Figure 8:
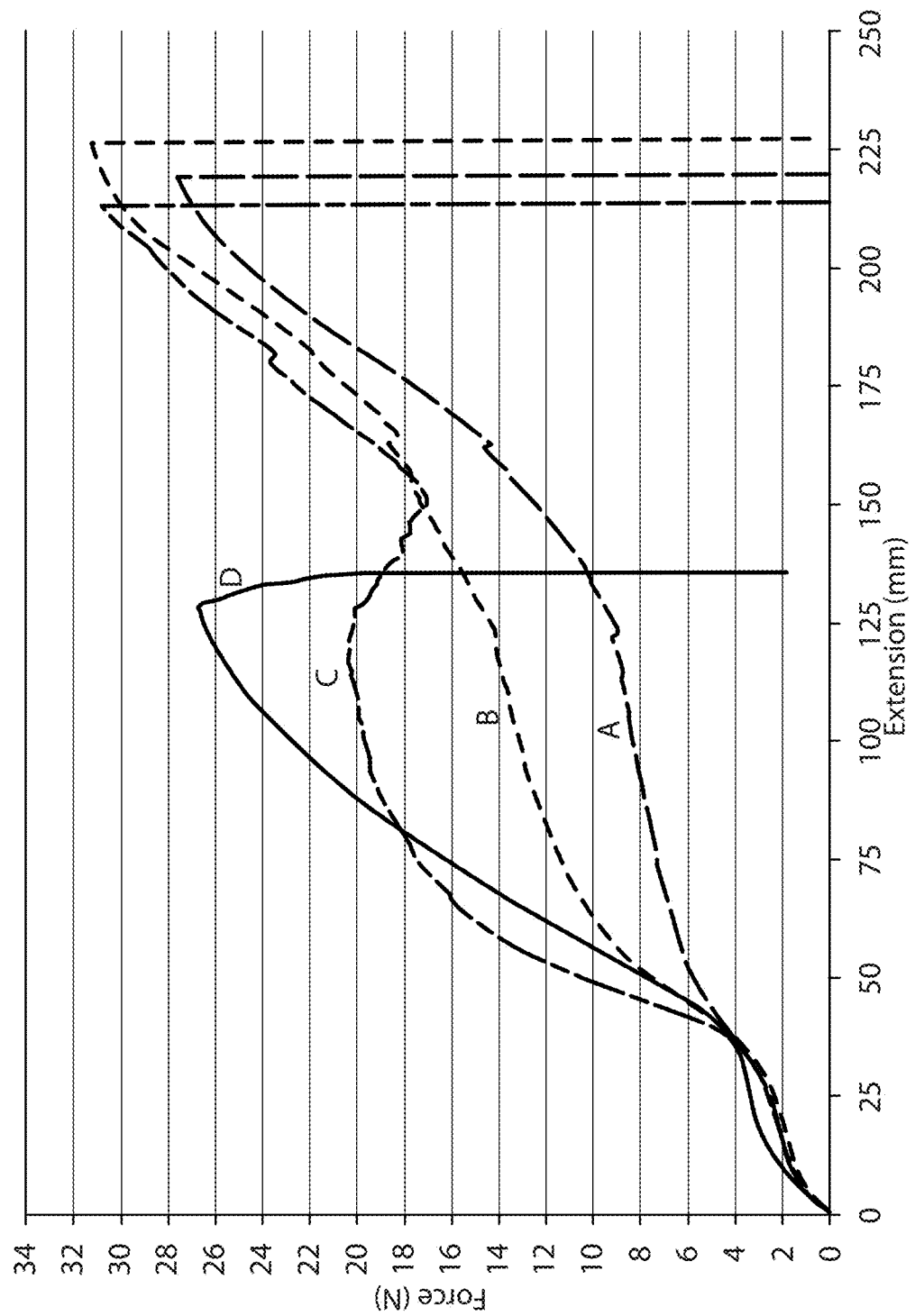
FIG. 8 is a chart depicting extensibility characteristics of exemplary laminates.

FIG. 8 and Table 2 below show a comparison of extension properties between laminates discussed below.

Comparative Example A is a ring-rolled activated laminate having an elastic film sandwiched between two nonwovens, where one nonwoven comprises a spunbond web and the other nonwoven comprises a carded web. The laminate layers are joined by adhesive. The laminate is commercially available from Clopay, USA under the trade name ElastiPro™ 8004. The laminate is void of crimped spunbond nonwoven webs.

Inventive Laminate Example B is a ring-rolled laminate having an elastic film adhesively bonded between two nonwovens. The first side is the nonwoven of Comparative Nonwoven Example 1 above. The second nonwoven comprises the crimped spunbond fiber nonwoven of Crimped Spunbond Fiber Nonwoven Example IV above. The elastic film has a basis weight of 50 gsm and is commercially available from Clopay, USA under the tradename ElastiPro™ 4407. The laminate layers are joined by adhesive H2031 available from Bostik, USA, applied at 12 gsm basis weight to create 1 mm on, 2 mm off, bead pattern with beads running in MD.

Inventive Example B laminate is ring-rolled activated using HSRP simulation with activation plates having intermeshing features with a tip radius of 0.1 mm, a root radius of 0.737 mm, ridge height of 25.4 mm, CD strain direction, depth of engagement of 6.5 mm, maximum average percent engineering strain of activation of 259% and target maximum activation strain rate of 442 sec$^{-1}$. One can use the ring-roll process with two rolls made with intermeshing grooves and ridges as in apparatus 400 in FIG. 6 to activate laminate and achieve the same resultant properties. Corresponding ring-roll process variables include roll diameter of 152.4 mm, web speed of 2.278 m/sec, and depth of engagement of 6.5 mm.

Inventive Laminate Example C is a ring-rolled activated laminate having an elastic film adhesively bonded between two nonwovens. Both nonwovens are the nonwoven of Crimped Spunbond Fiber Nonwoven Example IV. The elastic film has a basis weight of 50 gsm and is commercially available from Clopay, USA under the tradename ElastiPro™ 4407. The laminate layers are joined by adhesive H2031 available from Bostik, USA, applied at 12 gsm basis weight to create 1 mm on, 2 mm off, bead pattern with beads running in MD. The Inventive Laminate Example C is activated with the same HSRP equipment parameters used for activating laminate Inventive Laminate Example B above.

Inventive Laminate Example D is an ultrasonically bonded, gathered laminate having an elastic film sandwiched between two nonwovens as described in U.S. patent application Ser. No. 15/674,559. Both nonwovens are the nonwoven of Crimped Spunbond Fiber Nonwoven Example II above. The elastic film has a basis weight of 50 gsm and is commercially available from Clopay, USA under the tradename ElastiPro™ 4407.

Comparative Laminate Example E is an ultrasonically bonded, gathered laminate having an elastic film sandwiched between two nonwovens as described in U.S. patent application Ser. No. 15/674,559. Both nonwovens are the nonwoven of Example I above. The elastic film has a basis weight of 50 gsm and is commercially available from Clopay, USA under the tradename ElastiPro™ 4407.

Comparative Laminate Example F is a laminate having an elastic film adhesively bonded between two nonwovens. Both nonwovens are the nonwoven of Comparative Nonwoven Example I above. The elastic film has a basis weight of 50 gsm and is commercially available from Clopay, USA under the tradename ElastiPro™ 440. The laminate layers are joined by adhesive H2031 available from Bostik, USA, applied at 12 gsm basis weight to create 1 mm on, 2 mm off, bead pattern with beads running in MD. The laminate is not activated.

Inventive Laminate Example G comprises the same construction as Inventive Laminate Example C except the laminate has not yet been activated. The laminate comprises an elastic film sandwiched adhesively bonded two nonwovens. Both nonwovens are the nonwoven of Crimped Spunbond Fiber Nonwoven Example IV. The elastic film has a basis weight of 50 gsm and is commercially available from Clopay, USA under the tradename ElastiPro™ 4407. The laminate layers are joined by adhesive H2031 available from Bostik, USA, applied at 12 gsm basis weight to create 1 mm on, 2 mm off, bead pattern with beads running in MD.

Table 2 below shows extension properties of exemplary laminates. As can be seen from Table 5 and FIG. 8, the inventive ring-rolled activated laminates (Examples B and C) comprise comparable extension properties to Comparative Example A without having the more expensive carded nonwoven web in the laminate. The present invention achieves the desirable elastic laminate properties for absorbent article comfort and conforming fit at a much lower cost than incorporating carded nonwoven webs.

TABLE 2

Extension Properties of Exemplary Laminates

| Example | Extension at 2 N | Extension at 4 N | Average Peak Force at Break |
|---|---|---|---|
| Comparative Laminate Example A | 20.66 ± 0.58 mm | 38.23 ± 1.32 mm | 28.01 ± 0.25 N |
| Inventive Elastic Laminate Example B | 20.91 ± 1.92 mm | 38.44 ± 1.47 mm | 31.13 ± 0.62 N |
| Inventive Elastic Laminate Example C | 17.32 ± 0.93 mm | 35.61 ± 1.29 mm | 31.03 ± 1.95 N |
| Inventive Elastic Laminate Example D | 9.22 ± 0.68 mm | 35.45 ± 1.37 mm | 27.21 ± 1.46 N |

Tables 3 and 4 below show softness properties of nonwovens and laminates. As can be seen in Table 7, the Average TS7 and TS750 values of SS crimped fiber nonwoven webs are lower and thus more desirable than the Average TS7 and TS750 values of the nonwoven which is void of crimped nonwoven fibers. In addition, the Average TS7 values of the nonwoven remain similar when the nonwoven is incorporated into a laminate as shown in FIG. 4. Further, in certain embodiments, the elastomeric laminate comprises significantly lower TS7 values than laminates void of crimped spunbond fibers. Likewise, in certain forms such as an ultrasonically bonded laminate of the present invention, the laminate may comprise an Average TS750 value significantly lower than the Average TS750 values of laminates that are void of crimped spunbond fibers. This is important because the lower the TS7 and TS750 value, the softer the material will appear. Softness in absorbent articles is highly desirable given the tender care and attention needed for consumers using absorbent articles. Consumers might find absorbent articles with high TS7 and TS750 values uncomfortable and/or scratchy or otherwise undesirable.

TABLE 3

Softness Properties of Exemplary Nonwovens

| Example | Test Side | TS7 (dB V² rms) | TS750 (dB V² rms) |
|---|---|---|---|
| Comparative Nonwoven Example I (SSMMS) | Side 1 | 7.34 ± 1.29 | 13.60 ± 1.98 |
| | Side 2 | 7.66 ± 0.26 | 13.47 ± 1.19 |
| Crimped Spunbond Fiber Nonwoven Example II (SS Crimped) | Side 1 | 4.10 ± 0.25 | 3.36 ± 0.14 |
| | Side 2 | 4.82 ± 0.23 | 3.83 ± 0.36 |

TABLE 4

Softness Properties of Exemplary Laminates

| Example | Test Side | TS7 (dB V² rms) | TS750 (dB V² rms) |
|---|---|---|---|
| Inventive Laminate Example D (ultrasonically bonded, NW Example II on both sides) | Side 1 | 5.59 ± 0.45 | 72.68 ± 7.73 |
| | Side 2 | 4.85 ± 0.46 | 63.45 ± 14.55 |
| Comparative Laminate Example E (ultrasonically bonded, NW Example I on both sides) | Side 1 | 14.79 ± 2.53 | 146.40 ± 41.69 |
| | Side 2 | 12.83 ± 2.95 | 134.20 ± 25.63 |

TABLE 4-continued

Softness Properties of Exemplary Laminates

| Example | Test Side | TS7 (dB V² rms) | TS750 (dB V² rms) |
|---|---|---|---|
| Comparative Laminate Example F (adhesively bonded, NW Example I on both sides) | Side 1 | 11.18 ± 0.84 | 156.32 ± 34.42 |
| | Side 2 | 12.41 ± 0.91 | 203.57 ± 49.72 |
| Inventive Laminate Example G (adhesively bonded, NW Example IV on both sides) | Side 1 | 5.47 ± 0.69 | 215.82 ± 52.56 |
| | Side 2 | 4.44 ± 0.62 | 166.30 ± 19.44 |

The incorporation of a crimped spunbond fiber nonwoven web into a laminate or an absorbent article provides many additional advantages. Because the laminates of the present invention comprises at least one crimped spunbond fiber nonwoven web, the resultant nonwoven laminate has a higher caliper for a given basis weight. This higher caliper in turn delivers consumer benefits of comfort due to cushiony softness, faster absorbency due to higher permeability, and increased opacity. Additional benefits may include less redmarking, higher breathability and resiliency.

Additional benefits of utilizing crimped spunbond fiber nonwoven webs is that in some forms, particularly where the fibers comprise bi-component polypropylene/polypropylene, better bond strength can be achieved which makes this crimped spunbond fiber nonwoven web more abrasion resistant.

Even still more additional benefits of crimped spunbond fiber nonwoven webs include compatibility with like chemistries. For example, crimped spunbond fiber nonwoven webs comprising polypropylene/polypropylene bi-component fibers may be thermally joined (bonded) to subjacent materials in a disposable absorbent article which are polypropylene based. Also, the cost associated with polypropylene/polypropylene fibers can be less than the cost associated with other bi-component fibers. And, polypropylene/polypropylene fibers or fibers comprising two different polyesters may be recyclable versus bi-component fibers comprising polyethylene/polypropylene.

Regarding permeability, nonwoven laminates of the present invention, which include a crimped spunbond fiber nonwoven layer, have a higher permeability than nonwoven laminates which do not comprise a crimped spunbond fiber nonwoven layer.

Precursor Materials

The crimped spunbond fiber nonwoven web comprises constituent fibers. Such constituent fibers are randomly oriented and may comprise any suitable thermoplastic polymer. Some suitable thermoplastic polymers, as used in the disclosed compositions, are polymers that melt and then, upon cooling, crystallize or harden, but can be re-melted upon further heating. Suitable thermoplastic polymers used herein have a melting temperature (also referred to as solidification temperature) from about 60° C. to about 300° C., from about 80° C. to about 250° C., or from 100° C. to 215° C. And, the molecular weight of the thermoplastic polymer should be sufficiently high to enable entanglement between polymer molecules and yet low enough to be melt spinnable.

The thermoplastic polymers can be derived any suitable material including renewable resources (including bio-based and recycled materials), fossil minerals and oils, and/or biodegradeable materials. Some suitable examples of thermoplastic polymers include polyolefins, polyesters, polyamides, copolymers thereof, and combinations thereof.

Some exemplary polyolefins include polyethylene or copolymers thereof, including low density, high density, linear low density, or ultra-low density polyethylenes such that the polyethylene density ranges between 0.90 grams per cubic centimeter to 0.97 grams per cubic centimeter, between 0.92 and 0.95 grams per cubic centimeter or any values within these ranges or any ranges within these values. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof can also be used. Polypropylene copolymers, especially ethylene can be used to lower the melting temperature and improve properties. These polypropylene polymers can be produced using metallocene and Ziegler-Natta catalyst systems. These polypropylene and polyethylene compositions can be combined together to optimize end-use properties. Polybutylene is also a useful polyolefin and may be used in some embodiments. Other suitable polymers include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate); olefin carboxylic acid copolymers such as ethylene/acrylic acid copolymer, ethylene/maleic acid copolymer, ethylene/methacrylic acid copolymer, ethylene/vinyl acetate copolymers or combinations thereof; poly-lactic acid; polyacrylates, polymethacrylates, and their copolymers such as poly(m-ethyl methacrylates).

Non-limiting examples of suitable commercially available polypropylene or polypropylene copolymers include Basell Profax PH-835 (a 35 melt flow rate Ziegler-Natta isotactic polypropylene from Lyondell-Basell), Basell Metocene MF-650W (a 500 melt flow rate metallocene isotactic polypropylene from Lyondell-Basell), Polybond 3200 (a 250 melt flow rate maleic anhydride polypropylene copolymer from Crompton), Exxon Achieve 3854 (a 25 melt flow rate metallocene isotactic polypropylene from Exxon-Mobil Chemical), Mosten NB425 (a 25 melt flow rate Ziegler-Natta isotactic polypropylene from Unipetrol), Danimer 27510 (a polyhydroxyalkanoate polypropylene from Danimer Scientific LLC), Dow Aspun 6811A (a 27 melt index polyethylene polypropylene copolymer from Dow Chemical), Eastman 9921 (a polyester terephthalic homopolymer with a nominally 0.81 intrinsic viscosity from Eastman Chemical), Achieve 3155 (a 35 melt flow rate zinc isotactic polypropylene from Exxon Mobil).

The thermoplastic polymer component can be a single polymer species as described above or a blend of two or more thermoplastic polymers as described above, e.g. two different polypropylene resins. As an example, the constituent fibers of the first layer can be comprised of polymers such as polypropylene and blends of polypropylene and polyethylene. The nonwoven webs may comprise fibers selected from polypropylene, polypropylene/polyethylene blends, and polyethylene/polyethylene terephthalate blends. In some forms, the nonwoven webs may comprise fibers selected from cellulose rayon, cotton, other hydrophilic fiber materials, or combinations thereof.

For the nonwoven of the present invention, layers of the web which do not comprise the crimped spunbond fibers may comprise any of the above fibers. Additionally, such layers may comprise monocomponent fibers as well.

The fibers of the crimped spunbond fiber nonwoven webs of the present invention may comprise fibers which are bi-component, multi-component, and/or bi-constituent, round or non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >2 denier), shape (i.e. capillary and round) and the like. The constituent fibers can range from about 0.1 denier to about 100 denier, or from about 0.5 denier to about 25 denier, or about 1 denier, or about 1.5 denier, or about 1.7 denier, or about 2 denier, or about 2 denier or less.

Figure 9:
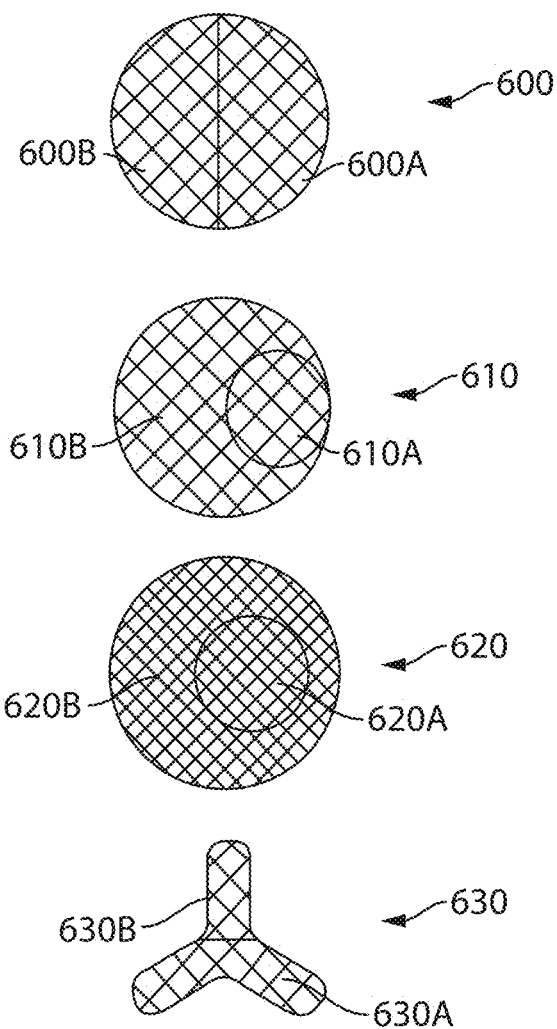
FIG. 9 is a schematic illustration of multiple cross sections of bi-component fibers for use with the present invention.

Some suitable examples of bi-component fiber configurations are shown in FIG. 9. For example, fibers of the crimped spunbond fiber nonwoven webs of the present invention may comprise fibers having a cross section 600 which comprises a first component 600A and a second component 600B arranged in a side by side configuration. As another example, crimped spunbond fiber nonwoven webs of the present invention may comprise fibers having a cross-section 610 which comprises a first component 610A and a second component 610B in an eccentric sheath-core configuration. Another eccentric sheath-core configuration which may be utilized is shown with regard to cross-section 620 which comprises a first component 620A and a second component 620B. Also, non-round fiber cross-sections are contemplated. For example, the crimped spunbond fiber nonwoven webs of the present invention may comprise fibers having a cross-section 630 which is tri-lobal. The tri-lobal cross section 630 comprises a first component 630A and a second component 630B, where the second component 630B is one of the lobes of the tri-lobal cross section.

Some specific examples of fibers which can be used in the crimped spunbond fiber nonwoven webs of the present invention include polyethylene/polypropylene side-by-side bi-component fibers. Another example, is a polypropylene/polyethylene bi-component fiber where the polyethylene is configured as a sheath and the polypropylene is configured as a core within the sheath. Still another example, is a polypropylene/polypropylene bi-component fiber where two different propylene polymers are configured in a side-by-side configuration. Still another example, is polypropylene/poly-lactic acid bi-component fiber. Still another example is polyethylene/poly-lactic acid bi-component fiber. For the bi-component fibers of polyethylene/poly-lactic acid, such fibers may be produced from renewable resources. For example, both the polyethylene and polylactic acid may be bio sourced. Additionally, polypropylene and poly-lactic acid based fibers would typically not withstand the out-of-plane deformation processing described herein; however, when configured as a crimped fiber, such fibers may withstand said processing.

Bi-component fibers may comprise two different resins, e.g. a first resin and a second resin. The resins may have different melt flow rates, molecular weights, branching, viscosity, crystallinity, rate of crystallization, and/or molecular weight distributions. Ratios of the 2 different polymers may be about 50/50, 60/40, 70/30, 80/20, 90/10 or any ratio within these ratios. The ratio may be selected to control the amount of crimp, strength of the nonwoven layer, softness, bonding or the like.

Bonding constituent fibers in the nonwoven can be important to achieve properties such as extensibility. For instance, optimally or ideally bonded webs may be desirable. Optimally or ideally bonded webs are characterized by the highest peak tensile strength and elongation at tensile peak with a rapid decay in strength after tensile peak. Such bonding allow for fibers to stretch and break around the bond sites when the web is strained beyond a certain point.

Further, if the calendar bond area is too low, a web with low strength and poor abrasion resistance may result. However, if the calendar bond area is too high, the length of fibers between bonds may be reduced which inhibits the amount of uncoiling and/or displacement possible. In such configurations, the crimped fibers must undergo plastic deformation or break once the amount of uncoiling surpasses the amount of applied process strain. In some forms of the present invention, the crimped spunbond fiber nonwoven webs may comprise a calendar bond area of between about 10% to about 20%, or about 12% to about 18% or any value within these ranges. A calendar bond area above about 10 percent and less than about 18 percent allows for a good balance of fiber mobility and free fiber length available for uncoiling but still provides sufficient strength in the crimped spunbond fiber nonwoven web for manipulations of the crimped spunbond fiber nonwoven web as well as abrasion and tearing resistance in use.

The size of each individual fusion bond nub may range from 0.5 mm$^2$ to 5 mm$^2$, 1 mm$^2$ to 3 mm$^2$. The spacing between fusion bond nubs can range from 1 mm to 5 cm, 1.6 mm to 3 cm. The bonds can be shaped like dots, diamonds, ovals or any other suitable shape and may be arranged in any suitable pattern to provide the desired mechanical properties.

Extensibility of crimped spunbond fiber nonwoven webs also can be impacted by the degree of crimp in the constituent fibers. The more curl that the fibers comprise, the higher the tensile elongation of the crimped spunbond fiber nonwoven web. The level of curl of a crimped spunbond fiber nonwoven web can be tailored based upon material selection, ratio of the two polymers of the bi-component fiber, fiber cross section, amount of draw in the spunbond process, heat treatments, and melt additives. Additionally, with a narrower molecular weight distribution in the material selection, more crimp can be achieved.

In some forms, nonwoven laminates of the present invention may be configured with constituent nonwoven webs which have differing levels of extensibility. For example, a lower layer may comprise a nonwoven having greater extensibility than an upper layer.

Further, the constituent nonwoven layers of the nonwoven webs of the present invention may be provided with structural integrity via a variety of different processes. Some examples include thermal point bonding, air through bonding, hydroentangling, and needlepunching each of which is well known in the art.

In some forms, the constituent fibers of the first nonwoven web are selected such that the first nonwoven web is hydrophobic, and the constituent fibers of the second nonwoven web are selected such that the second nonwoven web is hydrophilic.

As noted previously, some laminates of the present invention may additionally comprise film. Any suitable film may be utilized. Suitable elastomeric films are discussed above. Where laminates comprising film are utilized, the film may be extruded directly onto the crimped spunbond fiber nonwoven web during the making of the laminate. In alternative embodiments, the film may be provided as a separate component and joined to one or more nonwoven webs via adhesive bonding, ultrasonic bonding, or any other suitable bonding mechanism.

Additives

One or more layers of the nonwoven web may comprise additives. For instance, a first layer hydrophobic melt additive and/or the second layer may include a hydrophilic melt additive or topical hydrophilic. Additives may be used to modify coloration, antistatic properties, lubrication, softness, hydrophilicity, hydrophobicity and the like and combinations thereof. These additives, for example titanium dioxide for coloration, are generally present in an amount less than about 5 weight percent and more typically about 2 weight percent or less.

A suitable example of an additive for softness includes Erucamide which may be provided in amounts ranging from about 1 to about 20 percent by weight.

Some suitable examples of hydrophilic additives include: Techmer PPM15560; Techmer TPM12713; Polyvel VW351 PP Wetting Agent; Goulston Hydrosorb 1001; as well as those hydrophilic additive disclosed in US Patent Application Publication No. 2012/0077886. Some suitable examples of post formation additives include Silastol PH26, PHP90 or PST-N available from Schill & Seilacher, or Stantex 56327 available from Pulcra Chemicals GmbH.

Some examples of suitable hydrophobic additives include fatty alcohols and fatty acid esters. Nonlimiting examples of suitable fatty alcohols having from about 12 to about 24 carbon atoms include saturated, un-substituted, monohydric alcohols or combinations thereof, which have a melting point less than about 110° C., preferably from about 45° C. to about 110° C. Specific examples of fatty alcohol carriers for use in the skin care compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol are Stenol 1822 and behenyl alcohol is Lanette 22, both of which are available from the Cognis Corporation located in Cincinnati, Ohio. Non-limiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Non-limiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Figure 10:
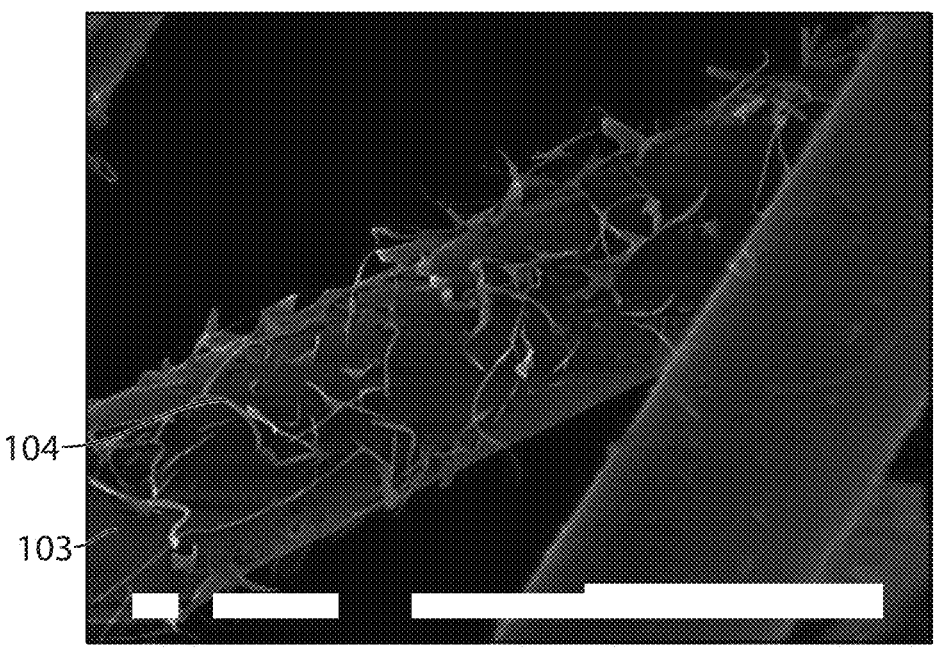
FIG. 10 is a scanning electron micrograph ("SEM") photo showing a nonwoven fiber with additive that has bloomed on the surface of the fiber.

In some forms, the additive may be added directly to the fibers or as master batch to the polymer melt during spinning of the filaments as a melt additive. Where the additive is melt blended into the filaments, the additive can bloom to the surface of the fibers and create a film covering a portion of the external surface of the fiber and/or can create fibrils, flakes, particles, and/or other surface features. For those fibers comprising fibrils 104, the fibrils may extend outwardly, or radially outwardly, from the surface as shown in FIG. 10. Fibrilization may result in increased opacity, providing a more finished look to the laminate and preventing the perception of defects from being able to view skin or interior components through the laminate. Further, without wishing to be bound by theory, it is believed that the additive, regardless of whether a melt additive or applied post fiber production, changes the surface energy of the constituent fibers. The change in surface energy increases the hydrophobic nature of the constituent fibers and therefore the nonwoven web. Additionally, it is believed that the additive, whether a melt additive or applied post fiber production, increases the surface roughness of the constituent fibers which can increase hydrophobicity. Thus, the additives may increase the hydrophobicity of the fibers upon whose surface they bloom.

Fibrils or flakes or other surface structures protruding from surface due to blooming may be of the order of few nanometers to few tens of micrometers. For example, the average length of the bloomed surface structures can range from about 5 nanometers to about 50 micrometers, from about 100 nanometers to about 30 micrometers, or from about 500 nanometers to about 20 micrometers. Preferred average width of the bloomed surface structures can range from about 5 nanometers to about 50 micrometers, from about 100 nanometers to about 20 micrometers, or from about 500 nanometers to about 5 micrometers. Preferred average thickness of the bloomed surface structures would range from about 5 nanometers to about 10 micrometers, more preferably from about 50 nanometers to about 5 micrometers, and most preferably from about 100 nanometers to about 1 micrometers. Preferred average hydraulic diameter, calculated as 4*(Cross-sectional Area)/(Cross-sectional Perimeter) of the bloomed surface structure can range from about 5 nanometers to about 20 micrometers, from about 50 nanometers to about 10 micrometers, or from about 100 nanometers to about 1.5 micrometers. In a specific embodiment, the average hydraulic diameter of a fibril is in the range of from about 100 nanometers to about 800 nanometers. Average separation of the bloomed surface structures from one another can range from about 100 nanometers to about 20 micrometers, from about 500 nanometers to about 10 micrometers, or from about 500 nanometers to about 5 micrometers.

The crimped spunbond fiber nonwoven webs of the present disclosure or crimped spunbond fiber nonwoven laminates of the present disclosure that have at least one layer comprising fibers comprising fibrils may be configured to be softer or harder than, or have the same softness as, conventional nonwoven laminates and/or may have a rougher, smoother, or the same tactile property as compared to conventional nonwoven substrates. The softness, hardness, and/or tactile property of the nonwoven substrates may vary depending on the type and amount of lipid esters present in the composition used to form the fibers and the length of the fibrils, for example. The softness, hardness, and/or texture may also vary depending on where the one or more layers of fibers having fibrils are positioned within a nonwoven substrate.

The additive may be applied at a basis weight of from about 0.1 gsm to 10 gsm, preferably <1 gsm or alternatively 0.4 percent by weight. The additive may be blended with other melt additive or topical ingredients, for example in a lotion composition. For those forms where bi-component fibers are utilized, the additive may be present at the same level in each of the constituents of the bi-component fiber, may be at different levels with regard to the constituents of the bi-component fiber, or may be preset in one constituent but not the other of a bi-component fiber.

For those forms where the hydrophobic additive is provided as a melt additive, e.g. part of the master batch, the additive may be present preferably between 0.5 percent by weight to about 20 percent by weight, preferably less than 10 percent by weight or any range within these values or any value within these ranges.

The additive may be applied to the fibers of the nonwoven laminates of the present invention by any suitable process. Some examples include spraying, slot coating, or the like. Other suitable hydrophobic additives are available from Techmer PM, LLC.

Opacity

The opacity of the crimped spunbond fiber nonwoven webs may differ from the opacity of adjacent layers of an absorbent article. In some instances, the crimped spunbond fiber nonwoven web may form a wearer-facing surface which is closest to an external observer. In such instances, the web comprising the crimped spunbond fibers may have a lower opacity than an underlying layer in order to maximize observable contrast differences between the layers and/or to observe printing or colored adhesives. In some forms, the crimped spunbond fiber nonwoven webs may have a low opacity in the context of an absorbent article outer cover such that graphics on subjacent layers may be visible therethrough.

Alternatively, the crimped spunbond fiber nonwoven web as part of the wearer-facing surface may have a higher opacity than an underlying layer in order to more effectively mask bodily exudates (e.g., urine, menses, or BM), to provide for greater color contrast with the layers below, or to inhibit viewing through the layer to underlying layers and/or skin. In a form, where the crimped spunbond fiber nonwoven web is located on the external surface of an absorbent article (e.g., an outer cover, fastening system element, stretch ear, belt, or side panel), the layer closest to an external observer would be the garment-facing surface.

As noted, crimped spunbond fiber nonwoven web of the present invention may have a high opacity. To achieve this benefit, opacities of greater than about 30, about 40, about 50, or about 60 may be desired. In some forms of the present invention, opacities may range from about 40-100 or from about 50-90, specifically reciting all values within these ranges and any ranges created thereby.

Increases in opacity can be achieved via any known suitable product/process. Some suitable examples include adding fillers (e.g. TiO2), fiber shape (e.g. tri-lobal vs. round), smaller fiber diameters (including microfibers and/or nano fibers), etc. A specific example of nonwoven web having high opacity is an SMS (spunbond, meltblown, spunbond) or an SMNS (spunbond, meltblown, nano fiber, spunbond) construction. Another specific example is a nonwoven comprising nano fibers, such as those produced by melt film fibrillation as described in U.S. Pat. No. 8,487,156 and U.S. Patent Application Publication No. 2004/0266300. In one specific example, the web of the invention may comprise a layer having meltblown and nanofibers—SMNS construction.

Absorbent Article

Absorbent articles of the present invention may utilize the crimped spunbond fiber nonwoven webs described herein in any suitable location. In certain embodiments, a nonwoven web comprising one or more crimped spunbond fiber layers is present in an ear 30 or side panel of a disposable article.

Figure 11:
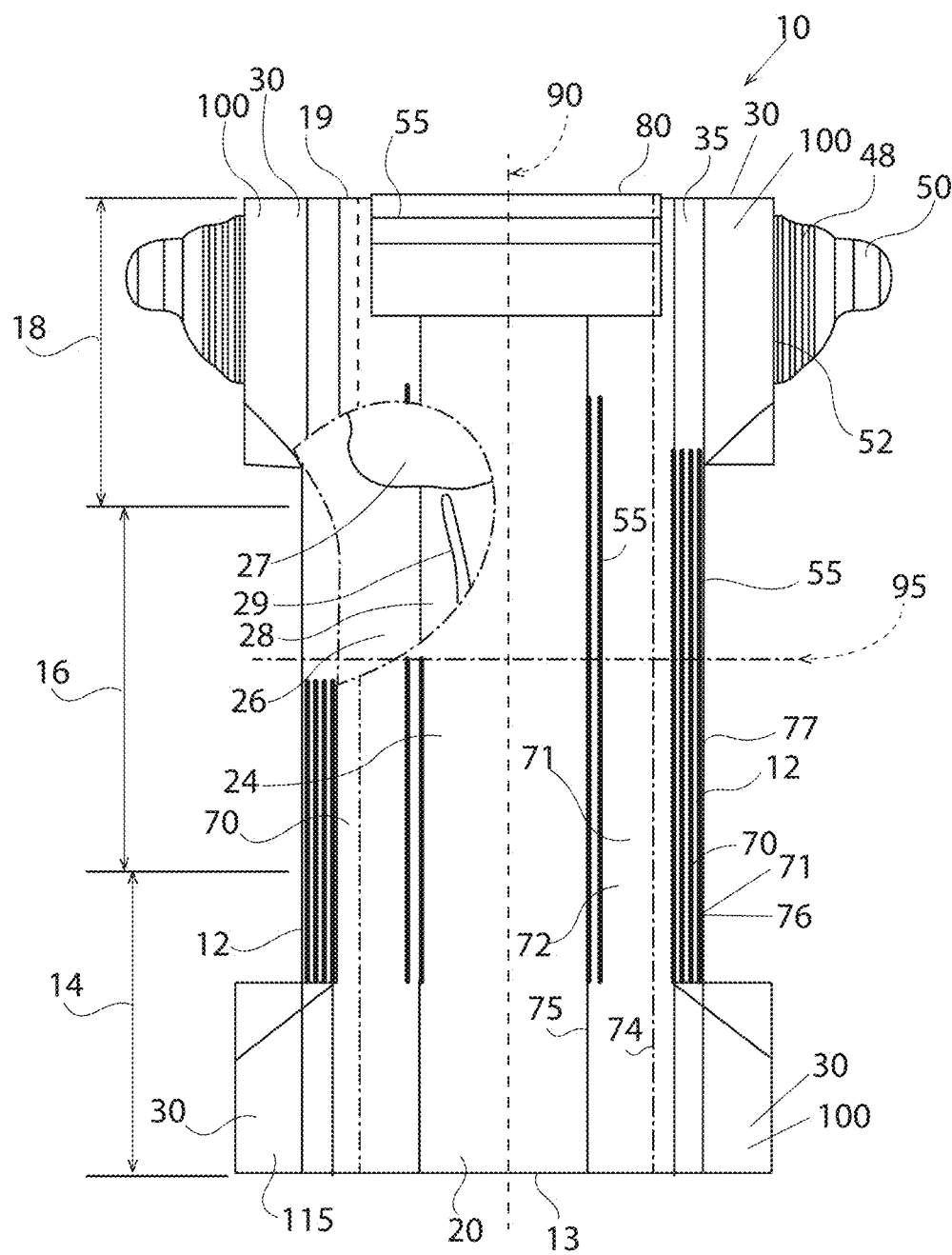
FIG. 11 is a top view of an absorbent article with some layers partially removed in accordance with the present disclosure.

FIG. 11 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 90 and a lateral centerline 95.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635, 191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In one nonlimiting example, two channels are symmetrically disposed about the longitudinal axis.

Exemplary absorbent structures for use as the absorbent core 28 are described in U.S. Pat. Nos. 4,610,678; 4,673, 402; 4,834,735; 4,888,231; 5,137,537; 5,147,345; 5,342, 338; 5,260,345; 5,387,207; 5,397,316, and U.S. patent application Ser. Nos. 13/491,642 and 15/232,901.

Backsheet:

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 10 may include one or more ears 30, including for example front ears disposed in the first waist region and/or back ears disposed in the second waist region. The ears 30 may be integral with the chassis or discrete elements joined to the chassis 20 at a chassis attachment bond 35, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

As illustrated in FIG. 5, ears may include a distal edge 36 and a proximate edge 38. The distal edge 36 is the free distal longitudinal edge of the ear. The proximate edge 38 is substantially opposed to the distal edge 36. The proximate edge 38 is joined to or overlapped with the chassis when the ear is joined to the chassis, or is the side defined by a line extending from longitudinal side 12 in the widest area of the crotch region and running parallel to the longitudinal centerline in the case of integral ears. Ears may further include a first lateral edge 40 and an opposing second lateral edge 42. An ear may additional comprise a maximum width, W, extending between the distal edge and proximate edge and a length, L, extending between the first and second lateral edges. In some instances, the length may vary at portions along the width of the ear, as shown in FIG. 5. For instance, the ear may comprise a maximum length along its proximate edge 38 and slope or otherwise vary such that the ear comprises a minimum length on its distal edge 36.

In some embodiments, the ear 30 may include elastomers, such that the ear is stretchable. In certain embodiments, the ears 30 may be formed of a stretch laminate such as a nonwoven/elastomeric material laminate or a nonwoven/ elastomeric material/nonwoven laminate, which also results in the ear being stretchable. The ear 30 may be laterally-extensible. In some embodiments, the ear is elastic when stretched in the lateral direction. In further embodiments, the ear 30 may extend more in the lateral direction than in the longitudinal direction. Alternatively, the ear may extend more in the longitudinal direction than in the lateral direction.

In some embodiments, the ear comprises a laminate of a first nonwoven 300 and an elastomeric layer 304. In certain embodiments illustrated in FIGS. 4-5, an ear comprises a first nonwoven 300, a second nonwoven 302 and an elastomeric layer 304. The elastomeric layer 304 may be sandwiched between the first and second nonwovens. Additional layers may be included (e.g., additional nonwovens, inelastic materials, elastic or extensible materials, etc.). An ear 30 may comprise one or more nonwoven webs comprising crimped spunbond fibers, as detailed above.

The absorbent article 10 may also include a fastening system 48. When fastened, the fastening system 48 interconnects the first waist region 16 and the rear waist region 18 resulting in a waist circumference that may encircle the wearer during wear of the absorbent article 10. The fastening system 48 may comprise a fastening elements 50 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 48 and/or the element 50 is foldable.

The fastening system 48 may be joined to any suitable portion of the article 10 by any suitable means. In some embodiments, the fastening system is joined to the ear 30 at a fastener attachment bond 52. The fastening system may be joined to the ear between layers, or joined to the ear on an exterior surface of the ear, or joined to a body-facing surface of the ear or a garment facing surface. In one nonlimiting example, the fastening system 48 and/or fastening elements 50 are ultrasonically bonded to the ear 30. The nonwoven layer(s) of the ear 300, 304 may be folded at the fastening attachment bond and/or at the side of the ear where the fastening system is attached. The fastening attachment bond 52 comprises a maximum length, measured parallel to the longitudinal centerline. The maximum length may be about 30 mm or less, or about 28 mm or less, or from about 20 mm to about 35 mm, reciting for said range every 1 mm increment therein. The fastening attachment bond may join the fastening system to one or more layers of the ear.

The fastening system 48 may be joined to ear at the distal side 36. The fastening system may be disposed in the second inelastic region 312. In further embodiments, the fastening system 48 is joined in the elastic region 306 of the ear. Joining the fastening system to the ear in the elastic region 306 improves the overall strength of the ear/fastening system combination during use and/or application. Without being bound by theory, it is believed that breakage in ears formed from ultrasonically bonded laminates initially occurs in an inelastic region at the distal side 36 as the intact nonwoven resists the stretching of the elastomeric layer; and therefore, joining the fastening system within the elastic region 306 reduces the stress on the inelastic portion of the ear. In some embodiments, the fastening system 48 is joined in the elastic region such that it overlaps with the elastic region for a maximum lateral overlap distance of about 0.05% to about 5%, or about 1% to about 5% of Y (i.e., the maximum width of the elastic region), reciting for each range every 0.02% increment therein.

In certain embodiments, the ear may comprise an Breathability Value of at least about 1 $m^3/m^2$/min, or from about 1 $m^3/m^2$/min to about 125 $m^3/m^2$/min, or from about 2 $m^3/m^2$/min to about 50 $m^3/m^2$/min according to the Air Permeability Test Method herein, reciting for each range every 1 $m^3/m^2$/min increment therein.

Leg Gasketing System

Returning to FIG. 11, the absorbent article 10 may comprise a leg gasketing system 70 attached to the chassis 20, which may comprise one or more cuffs 71. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximate edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 90 and are at least present in the crotch region. The barrier leg cuffs may be joined at the proximate edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximate edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, 14/077,708; U.S. Pat. Nos. 8,939,957; 3, 860,003; 7,435,243; 8,062,279.

Elastic Waist Feature

The absorbent article 10 may comprise at least one elastic waist feature 80 that helps to provide improved fit and containment, as shown in FIG. 11. The elastic waist feature 80 is generally intended to expand and contract to dynamically fit the wearer's waist. Elasticized waist features include waistbands, waist cuffs having pockets formed from a portion of the waist feature 80 that is unattached from the chassis 20, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 20 in the first waist region 14 and/or in the second waist region 16. The waist feature can be used in conjunction with the ear 30 to provide desirable stretch and flexibility for proper fit of the article on the wearer.

Packages

Absorbent articles comprising the crimped spunbond fiber nonwoven web or laminate of the present invention may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 12:
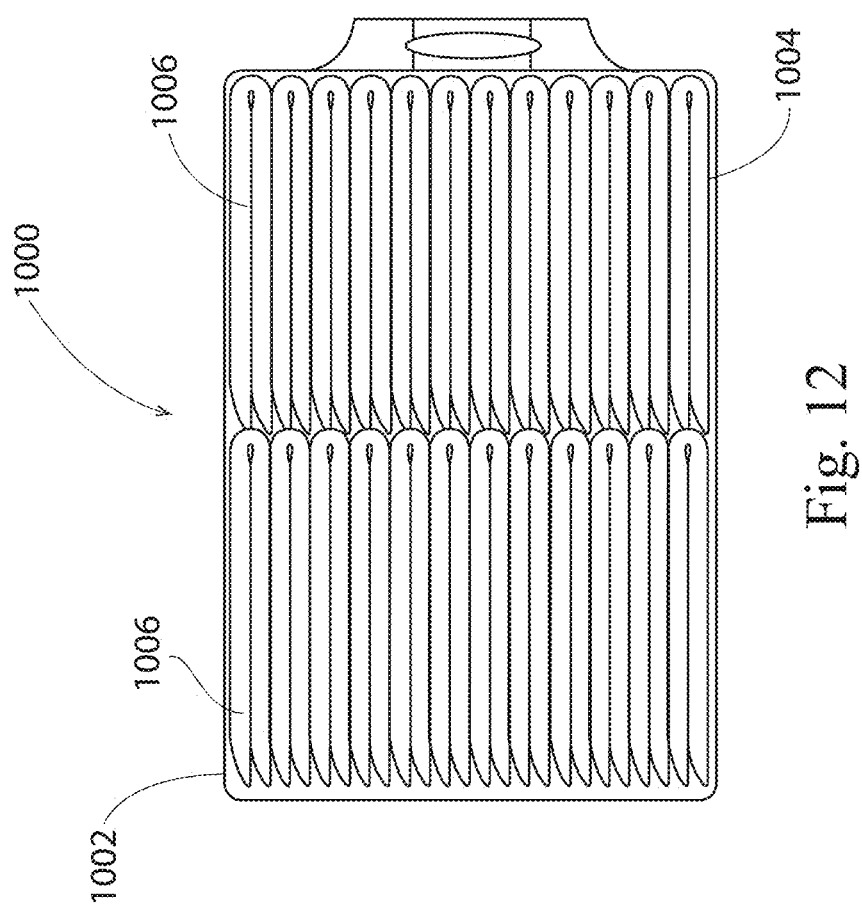
FIG. 12 is a schematic representation of a stack of absorbent articles within a package.

FIG. 12 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods

Opacity Method

Opacity by contrast ratio measurements are made using a 0°/45° spectrophotometer suitable for making standard CIE L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2 C.° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors carefully excise the specimen from the article for testing. Place the specimen flat against the instrument with the outward facing surface toward the spectrophotometer's measurement port and the region of interest within the port. Ensure that no tears, holes or apertures are within the measurement port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicate specimens.

Opacity is calculated by dividing the Y value measured using the black tile as backing, divided by the Y value measured using the white tile as backing, then multiplying the ratio by 100. Record the opacity value to the nearest 0.01%. Calculate opacity for the 10 replicates and report the average opacity to the nearest 0.01%.

Basis Weight Test Method

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{(\text{Weight of the specimen in grams})}{(\text{Length of the specimen in meter})(\text{Width of the specimen in meter})}$$

For calculating the basis weight of a substrate, a total 8 rectilinear specimens at least 10 mm×25 mm are used.

The average basis weight and standard deviation are recorded.

Nonwoven specimens from absorbent articles are obtained as follows. The specimen web be taken from a region having no additional material (i.e., only nonwoven). Each nonwoven web is separated from the other layers of the laminate without damaging or tearing the nonwoven web. If one continuous nonwoven covers inelastic regions of the laminate, said nonwoven is separated from the inelastic regions and used as the specimen. If the nonwoven layer is inseparable from other laminate layers, the specimen is collected from the outermost inelastic region of the laminate (outermost relative to the article). If the outermost inelastic region is smaller than the prescribed specimen dimensions or has additional material (other than nonwoven webs), and if the inner inelastic region has identical nonwovens as the outermost inelastic region, then the specimen (either nonwoven web or the combination of nonwoven webs) is collected from the inner inelastic region. If the nonwoven webs in the inelastic region are identical and/or inseparable, then the calculated basis weight of the specimen is divided by the number of nonwoven webs to get the individual nonwoven basis weight.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 12). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Fiber Diameter and Denier Test

The diameter of fibers in a sample of a nonwoven substrate is determined by using a Scanning Electron Microscope (SEM) and image analysis software. A magnification of 500 to 10,000 times is chosen such that the fibers are suitably enlarged for measurement. The samples are sputtered with gold or a palladium compound to avoid electric charging and vibrations of the fibers in the electron beam. A manual procedure for determining the fiber diameters is used. Using a mouse and a cursor tool, the edge of a randomly selected fiber is sought and then measured across its width (i.e., perpendicular to fiber direction at that point) to the other edge of the fiber. For non-circular fibers, the area of the cross-section is measured using the image analysis software. The effective diameter is then calculated by calculating the diameter as if the found area was that of a circle. A scaled and calibrated image analysis tool provides the scaling to get actual reading in micrometers (μm). Several fibers are thus randomly selected across the sample of the nonwoven substrate using the SEM. At least two specimens from the nonwoven substrate are cut and tested in this manner. Altogether, at least 100 such measurements are made and then all data is recorded for statistical analysis. The recorded data is used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

Fiber Diameter in denier=Cross-sectional area (in m$^2$)*density (in kg/m$^3$)*9000 m*1000 g/kg.

For round fibers, the cross-sectional area is defined by the equation:

$$A = \pi * (D/2)^2.$$

The density for polypropylene, for example, may be taken as 910 kg/m$^3$.

Given the fiber diameter in denier, the physical circular fiber diameter in meters (or micrometers) is calculated from these relationships and vice versa. We denote the measured diameter (in microns) of an individual circular fiber as D.

In case the fibers have non-circular cross-sections, the measurement of the fiber diameter is determined as and set equal to the hydraulic diameter, as discussed above.

Extension Test Method

A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 50.8 mm width may be used. The grips are air actuated grips designed to concentrate the entire gripping force along a single line perpendicular to the direction of testing stress having one flat surface and an opposing face from which protrudes a half round (radius=6 mm, e.g. part number: 56-163-827 from MTS Systems Corp.) or equivalent grips, to minimize slippage of the sample. The load cell is selected so that the forces measured are between 10% and 90% of the capacity of the load cell used. The initial distance between the lines of gripping force (gauge length) is set at 25.4 mm. The load reading on the instrument is zeroed to account for the mass of the fixture and grips.

A specimen measuring 50 mm (along the CD of the web) by 25.4 mm (along the MD of the web) of a given elastic laminate web is delicately cut from the web. The specimen is mounted into the grips in a manner such that there is no slack and the load measured is between 0.00 N and 0.02 N. The specimen is mounted in the center of the grips, such that the specimen direction of stretching is parallel to the applied tensile stress.

The specimen is extended at 508 mm/min, with a data acquisition rate of at least 50 Hertz, until the specimen breaks, typically 600-1000% strain. The % strain is calculated from the length between grip lines L, and initial gauge length, L$_0$, using the following formula:

$$\% \text{ Strain} = \frac{(L - L_0)}{L_0} \times 100$$

Each specimen is pulled until it ruptures (i.e. the post peak force response reaches a value less than 10% of the peak force). Four specimens of each set are measured, and the arithmetic average Peak Force at Break (N), and the Extension (mm) at 2N and at 4N are also recorded. Break is defined as the point where the material fractures or ruptures, and force drops rapidly to zero value. A total of four (4) specimens are run for example. The Average Extension at 2N and 4N, Peak Force at Break, and standard deviation of at least 4 specimens are recorded. If, standard deviation recorded is higher than 10%, a new set of four specimens is run.

Tensile Test Method

Figure 14:
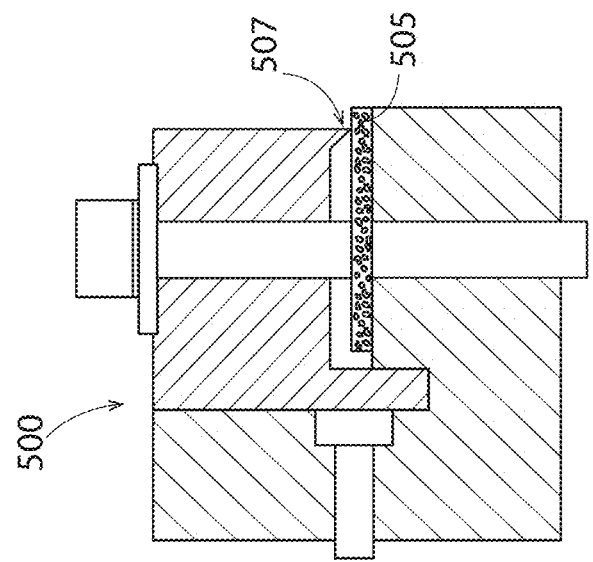
FIG. 14 is a schematic side elevation view of a grip suitable for use in the Tensile Test Method herein.
Figure 13:
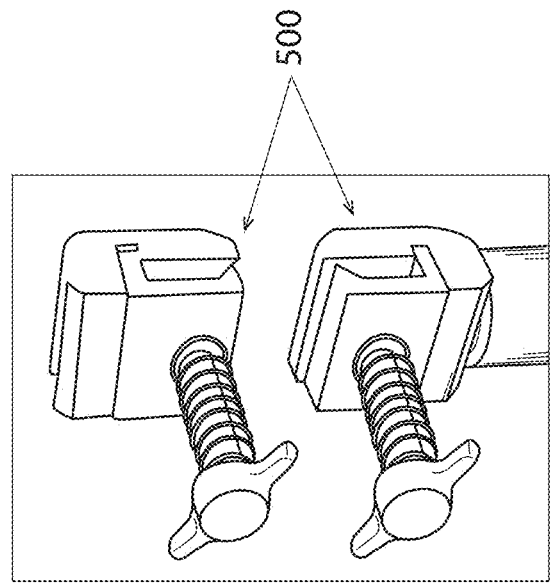
FIG. 13 is a schematic perspective view of grips suitable for use in the Tensile Test Method herein.

The Tensile Test is used to measure the strength of a specimen at a relatively high strain rate that represents product application. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Grips shown in the FIGS. 13 and 14 should be used to secure the specimens during tensile testing. (FIG. 14 is a side view of one of the grips in FIG. 13 with a material 505 to prevent slippage.) The opposing grips 500 may have the same width or different widths as specified.

(a) Grips

The line grips are selected to provide a well-defined gauge and avoid undue slippage. The specimen is positioned such that it has minimal slack and the specimen is centered between the grips. The apexes 507 of the grips are ground to give good gauge definition while avoiding damage or cutting of the specimen. The apexes are ground to provide a radius in the range of 0.5-1.0 mm. A portion of one or both grips may be configured to include a material 505 that reduces the tendency of a specimen to slip, (e.g., a piece of urethane or neoprene rubber having a Shore A hardness of between 50 and 70) as shown in FIG. 14. 154 mm wide top and bottom grips are used to clamp the specimen.

(b) Tensile Test of Specimen from Nonwoven Web

A specimen measuring 16.8 mm (along the cross machine (CD) of the web) by 127 mm (along the machine direction (MD) of the web) of a given nonwoven web is delicately cut from the web. For purposes of equations below, the specimen length is 16.8 mm and the specimen width is 127 mm. The specimen is tested as follows: The gauge length (i.e. clamp to clamp separation) of the vertical distance from the first grip location, to the second grip location is 10 mm, and is measured to 0.1 mm accuracy using a ruler. The specimen is tested at a test speed that provides a cross-head displacement speed of approximately 6 m/s. Before testing, 5 mm of slack is put between the grips. The specimen is placed between the grips 500 such that the CD of the specimen will be extended during the testing. In order to minimize the influence of the basis weight of each web sample being tested, each curve is normalized for the basis weight of the sample being tested (i.e. the values of the force applied are divided by the value of the basis weight of the web sample being tested), using the following formula:

$$\text{Normalized Force} \frac{N}{\frac{cm}{\frac{g}{m^2}}} = \frac{\left(\frac{\text{Force, N}}{\text{specimen width, cm}}\right)}{\left(\frac{\text{specimen mass, grams}}{(\text{specimen width, m}) \times (\text{specimen length, m})}\right)}$$

The strain of each sample is reported on the x axis in % Strain while the force applied to each sample is reported on the y axis in Normalized Force (N·m$^2$/g·cm). The % strain is calculated from the length between grip lines L, and initial gauge length, L$_0$, using the following formula:

$$\% \text{ Strain} = \frac{(L - L_0)}{L_0} \times 100$$

Each specimen is pulled until it ruptures (i.e. the post peak force response reaches a value less than 10% of the peak force). During testing, one of the grips is kept stationary and the opposing grip is moved. The force and actuator displacement data generated during the test are recorded using a MOOG SmarTEST ONE ST003014-205 standalone controller, with the data acquisition frequency set at 100 kHz. A total of five (5) specimens are run for example. The Average % Strain at Peak, Average Normalized Force at Peak in (N·m²/g·cm), and standard deviation of at least 5 specimens are recorded. If, standard deviation recorded is higher than 20%, a new set of five specimens is run. Peak is defined as the maximum force value followed by substantial drop in force. Break is defined as the point where the material fractures or ruptures, and force drops rapidly to zero value. % Strain at Peak is defined as the % Strain at the maximum force.

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut in dimension of 10 mm in the intended stretch direction of the laminate by 25.4 mm in the direction perpendicular to the intended stretch direction of the laminate. A specimen is collected from an inelastic region or an elastic region of the laminate (i.e., the sample does not cross into both inelastic and elastic regions).

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force. This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, Hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 100% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-/(l_{max}-l_{ini})*100\%$ to the nearest 0.01%. The testing is repeated for six separate samples and the average and standard deviation reported.

Softness Test Method

TS7 and TS750 values are measured using an EMTEC Tissue Softness Analyzer ("Emtec TSA") (Emtec Electronic GmbH, Leipzig, Germany) interfaced with a computer running Emtec TSA software (version 3.19 or equivalent). According to Emtec, the TS7 value correlates with the real material softness, while the TS750 value correlates with the felt smoothness/roughness of the material. The Emtec TSA comprises a rotor with vertical blades which rotate on the test sample at a defined and calibrated rotational speed (set by manufacturer) and contact force of 100 mN. Contact between the vertical blades and the test piece creates vibrations, which create sound that is recorded by a microphone within the instrument. The recorded sound file is then analyzed by the Emtec TSA software.

Sample Preparation

Test samples are prepared by cutting square or circular samples from a finished product. Test samples are cut to a length and width (or diameter if circular) of about 90 mm, and no greater than about 120 mm, in dimension. If the finished product has a discrete section of elastic region (i.e. elastic region is shorter in one or more dimensions than nonwoven facing-layers), a set of rectilinear specimens 76 mm±3 mm long in the primary stretch direction, and 100 mm±3 mm wide in the perpendicular direction is cut from the product part, with the elastic region centered in the rectilinear specimen. Test samples are selected to avoid creases or folds within the testing region, unless inherent to the sample such as corrugations. Prepare 8 substantially similar replicate samples for testing. Equilibrate all samples at TAPPI standard temperature and relative humidity conditions (23° C.±2 C.° and 50%±2%) for at least 1 hour prior to conducting the TSA testing, which is also conducted under TAPPI conditions.

Testing Procedure

Calibrate the instrument according to the manufacturer's instructions using the 1-point calibration method with Emtec reference standards ("ref.2 samples"). If these reference samples are no longer available, use the appropriate reference samples provided by the manufacturer. Calibrate the instrument according to the manufacturer's recommendation and instruction, so that the results will be comparable to those obtained when using the 1-point calibration method with Emtec reference standards ("ref.2 samples").

Mount the test sample into the instrument and ensure the sample is clamped into the TSA instrument properly with its first surface facing upwards. For samples with a discrete section of elastic region, ensure that the elastic region is centered below the Emtec vertical blades, and then perform the test according to the manufacturer's instructions. When complete, the software displays values for TS7 and TS750. Record each of these values to the nearest 0.01 dB $V^2$ rms. The test piece is then removed from the instrument and discarded. This testing is performed individually on the first surface of four of the replicate samples, and on the second surface of the other four replicate samples.

The four test result values for TS7 and TS750 from the first surface are averaged (using a simple numerical average); the same is done for the four test result values for TS7 and TS750 from the second surface. Report the individual average values and standard deviation of TS7 and TS750 for both the first and second surfaces on a particular test sample to the nearest 0.01 dB $V^2$ rms.

Air Permeability Test

The air permeability of a laminate or substrate (e.g., film, nonwoven) is determined by measuring the flow rate of standard conditioned air through a test specimen driven by a specified pressure drop. This test is particularly suited to materials having relatively high permeability to gases, such as nonwovens, apertured laminates and the like. ASTM D737 is used, modified as follows.

A TexTest FX 3300 instrument or equivalent is used, available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The specimen is tested while in a relaxed state.

The test pressure drop is set to 125 Pascal and the 38.3 $cm^2$ area test head (model FX 3300-5) or equivalent is used. The result is recorded to three significant digits. The average of 5 specimens is calculated and reported as the Air Permeability Value ($m^3/m^2/min$).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article comprising:
a chassis having a topsheet, backsheet and an absorbent core disposed between the topsheet and backsheet; and
an ear joined to the chassis, the ear comprising:
a ring-rolled laminate having a first nonwoven web and an elastomeric film, wherein the first nonwoven web comprises a crimped spunbond fiber nonwoven web, and wherein the ring-rolled laminate does not comprise any carded nonwoven webs.

2. The article of claim 1, wherein the laminate further comprises a second nonwoven web, and wherein the elastomeric film is disposed between the first nonwoven web and second nonwoven web.

3. The article of claim 2, wherein the crimped spunbond fiber nonwoven web comprises at least 80% crimped spunbond fibers by weight of the crimped spunbond fiber nonwoven web.

4. The article of claim 2, wherein the second nonwoven web comprises at least 80% crimped spunbond fibers by weight of the second nonwoven web.

5. The article of claim 1, wherein the first nonwoven web comprises a % Strain at Peak of about 50% or greater and an Average Normalized Force at Peak of about 0.17 $N·m^2/g·cm$ or less as determined by a defined Tensile Test Method.

6. The article of claim 1, wherein crimped spunbond fibers of the first nonwoven web comprise two different polypropylene polymers configured in a side-by-side configuration.

7. The article of claim 1, wherein the ring-rolled laminate comprises an Average Extension at 2N of about 5 mm or greater and an Average Extension at 4N of about 25 mm or greater according to a defined Extension Test Method.

8. The article of claim 1, wherein the laminate comprises an Average Peak Force at Break of about 20N or greater according to a defined Extension Test Method.

9. The article of claim 1, wherein the first nonwoven web comprises an additive for softness.

10. An article comprising:
a chassis having a topsheet, a backsheet and an absorbent core disposed between the topsheet and backsheet;
an ear joined to the chassis, the ear comprising:
a laminate having a first nonwoven web, a second nonwoven web, and an elastomeric film disposed between the first nonwoven web and second nonwoven web, wherein the laminate further comprises a plurality of ultrasonic bonds, wherein the first nonwoven web comprises a first crimped spunbond nonwoven web, and wherein the laminate does not comprise any carded non-woven webs.

11. The article of claim 10, wherein the laminate comprises an Extension at 4N of about 25 mm or greater according to a defined Extension Test Method herein.

12. The article of claim 10, wherein the first crimped spunbond nonwoven web comprises a bi-component fiber comprising polypropylene in a side-by-side configuration.

13. The article of claim 10, wherein the second nonwoven web comprises a second crimped spunbond nonwoven web.

14. The article of claim 10, wherein the first nonwoven web comprises an Average % Strain at Peak of about 50% or greater and an Average Normalized Force at Peak of about 0.17 N·m²/g·cm or less as determined by a defined Tensile Test Method.

15. The article of claim 10, wherein the laminate comprises an Average Peak Force at Break of about 20 N or greater according to a defined Extension Test Method.

16. The article of claim 10, wherein the laminate comprises Average Extension at 2N of about 5 mm or greater according to a defined Extension Test Method.

17. The article of claim 10, wherein crimped spunbond fibers of the first nonwoven web comprise two different polypropylene polymers configured in a side-by-side configuration.

18. The article of claim 10, wherein the first nonwoven web comprises an additive for softness.

* * * * *